(12) United States Patent
Nishimoto

(10) Patent No.: US 7,410,757 B1
(45) Date of Patent: Aug. 12, 2008

(54) METHOD OF SCREENING DISEASE DEPRESSANT GENE

(75) Inventor: Ikuo Nishimoto, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 10/088,699

(22) PCT Filed: Sep. 14, 2000

(86) PCT No.: PCT/JP00/06313

§ 371 (c)(1),
(2), (4) Date: Jun. 14, 2002

(87) PCT Pub. No.: WO01/21786

PCT Pub. Date: Mar. 29, 2001

(30) Foreign Application Priority Data

Sep. 17, 1999 (JP) ................... 11-264679
Jun. 29, 2000 (JP) ............................ 2000-201456

(51) Int. Cl.
*C12Q 1/68* (2006.01)
*C12N 15/85* (2006.01)

(52) U.S. Cl. .......................................... 435/6; 435/455
(58) Field of Classification Search ..................... 435/4, 435/6, 440, 455
See application file for complete search history.

(56) References Cited

FOREIGN PATENT DOCUMENTS

| EP | 0 616 032 A2 | 9/1994 |
|---|---|---|
| JP | 11-146743 | 6/1999 |
| JP | 11-146743 A | 6/1999 |
| WO | WO 00/14204 | 3/2000 |
| WO | WO 00/14204 A1 | 3/2000 |
| WO | WO 01/21787 | 3/2001 |
| WO | WO 01/21787 A1 | 3/2001 |

OTHER PUBLICATIONS

Giambarella et al. EMBO 16: 4897-4907, 1997.*
Nordquist et al. J. Neurscience 8: 4780-4789, 1988.*
Arriza et al. J. Neuroscience 12: 4045-4055, 1992.*
Saille, C. et al. Transgenic Murine Cortical Neurons Expressing Human Bcl-2 Exhibit Increased Resistance to Amyloid Beta-Peptide Neurotoxicity, Neuroscience 92(4):1455-1463, 1999.*
D'Adamio et al., "Functional cloning of genes involved in T-cell receptor-induced programmed cell death," *Seminars in Immunology*, 9:17-23 (1997).
Guo et al., "Calbindin D28k blocks the proapoptotic actions of mutant presenilin 1: Reduced oxidative stress and preserved mitochondrial function," *PNAS*, 95:3227-3232 (1998).
Vito et al., "Interfering with Apoptosis: Ca2+ -Binding Protein ALG-2 and Alzheimer's Disease Gene ALG-3," *Science*, 271:521-525 (1996).
Chiba et al., "Development of a Femtomolar-Acting Humanin Derivative Named Colivelin by Attaching Activity-Dependent Neurotrophic Factor to its N Terminus: Characterization of Colivelin-Mediated Neuroprotection against Alzheimer's Disease-Relevant Insults In Vitro and In Vivo," *Neurobiology of Disease*, 25(44): 10252-10261 (2005).

* cited by examiner

*Primary Examiner*—Nancy Vogel
(74) *Attorney, Agent, or Firm*—Townsend and Townsend and Crew LLP

(57) ABSTRACT

The present invention provides methods for screening and testing disorder suppressor genes and disorder suppressor polypeptides. By screening the cDNA expression library incorporated with nucleic acids derived from an organism suffering from a disorder that accompanies cell death, genes having suppressive effects on the disorder symptoms were successfully cloned. Furthermore, suppressive effects of the nucleic acid and polypeptide encoded by the nucleic acid on the disorder have been also examined. Screening of nucleic acids or polypeptides derived from an organism suffering from a disorder that accompanies cell death enables the efficient isolation and selection of suppressor genes of the disorder.

5 Claims, 18 Drawing Sheets

METHOD OF SCREENING DISEASE DEPRESSANT GENE

TECHNICAL FIELD

The present invention relates to a method of screening for a disorder suppressor gene or a disorder suppressor polypeptide.

BACKGROUND ART

Current progress in human genome analysis has lead to the identification of genes associated with a variety of disorders. The analyses of these disorder-associated genes are revealing complicated relationships between the actions of causative gene(s) (or the aberrant action of normal genes associated with disorders) and the action of gene(s) that suppress disorders. That is, almost all the disorders occurring in humans are thought to be caused by a collapse in the balance between the action of disease-causing aberrant genes (or aberrant action of normal genes associated with disorders) and the action of normal suppressor genes that compete with aberrant genes. Such a view-point may be applicable to almost all the disorders ranging from stomach ulcer to neurodegenerative diseases, indicating, in other words, a possible presence of normal genes that suppress a majority of disorders (or disorder suppressor genes) in the genome. Needless to say, development of an efficient method of screening for such genes undoubtedly would enable the discovery and identification of useful genes expressing specific therapeutic effects on a variety of human disorders, including intractable diseases for which no treatment has yet been found.

Conventionally, a suppressor gene for a particular disorder was screened mostly by using a method that searched for a molecule that suppressed a biochemical function of a causative gene using the biochemical function as an index. However, such a method cannot be applied to cases where the biochemical function of the causative gene has not been elucidated. Furthermore, even if the biochemical function has been identified, the search for drugs based on the function may not directly lead to a molecule capable of curing the disorder when the biochemical function is not the direct cause of the onset of the disorder. In fact, even if a gene has been proved to be a causative of a particular disorder from epidemiological, genetic, or other studies, the biochemical function of the gene cannot be often identified, and, moreover, even if it is identified, it is difficult to clarify whether the identified function is the direct cause for the onset of the disorder. For example, although it has been demonstrated that a mutation in the α-synuclein gene, which has been identified as one of the Parkinson's disease (PD)-associated genes (Polymeropoulos, M. H. et al., 1997, Science 276: 2045-2047), is definitely the gene that causes the onset of PD, the biochemical function of α-synuclein has not so yet been elucidated. An Alternative example is the ATM gene, causative of ataxia telangiectasia (spinocerebellar degeneration with capillarectasia), in which although the only known biochemical function of ATM is a PI3 kinase-like activity, it is entirely unclear whether the aberration of this biochemical function causes the onset of the disorder. Thus, it is extremely difficult to develop a therapeutic molecule for a disease based on the mere identification of a causative gene.

Systems that attempt screening through a more functional method have been developed. One of them is a method of screening for genes and molecules that suppress cell death induced by disease-causing genes, which has been conventionally referred to as the death-trap method (D'Adamio, L. et al., Semin. Immunol. 1997, 9: 17-23). However, due to the extremely low efficiency in screening when using only the conventional death-trap method, this method has not so far become an effective screening method.

As described above, almost all the disorders occurring in humans are thought to be caused by a collapse in the balance between the action of disease-causing aberrant genes (or aberrant action of normal genes associated with disorders) and the action of normal suppressor genes that compete with aberrant genes. Therefore, it is highly likely that suppressor genes for a majority of disorders are present in the genome. Thus, screening of a cDNA library covering the human genome using the death-trap method may theoretically lead to the discovery of disorder suppressor genes. However, it is extremely difficult to discover such a suppressor gene out of the vast genome even by conducting this screening method, and in fact, no disorder suppressor gene has so far been found using the death-trap method even several years after its establishment. Therefore, a method capable of more efficiently screening disorder suppressor genes has been anticipated.

DISCLOSURE OF THE INVENTION

An objective of the present invention is to provide a method for efficiently screening for a disorder suppressor gene or disorder suppressor polypeptide. Furthermore, another objective of this invention is to provide a method for testing disorder suppressor genes or polypeptides.

To solve the above-described issues, the present inventor aimed to develop a method for efficiently screening for a suppressor gene for a disorder in which cell death is a pathological feature (cell death can be the main or a part of the pathological state), that is, a disorder that accompanies cell death. For a more efficient screening of a disorder suppressor gene, the present inventor thought it important to use a more condensed group of candidate disease suppressor genes rather than merely using a cDNA library. In disorders that accompany cell death, a pathological feature is the degeneration of cells in affected areas of organs or tissues in which cell death occurs. Usually, such diseased organs and tissues may not be suitable objects for screening for a disorder suppressor gene, even though they can be objects for screening for a disease-causing factor. In this regard, the present inventor focused their attention on the fact that in disorders accompanying cell death, cell death does not necessarily occur in all the cells contained in the affected area. They also thought that, in the relatively slightly affected tissues as well as normal tissues in the vicinity of the affected area, the disease-causing factor is not necessarily absent, but pathological symptoms may not have developed in spite of the presence of the causative factor. That is, although it appears natural that normal tissues do not develop pathological symptoms, tissues in the vicinity of the affected area may sufficiently express a disorder suppressor gene preventing the development of pathological symptoms. Based on such a concept, it should be able to construct a condensed library of disease-suppressor genes by preparing mRNA from the affected area or tissues in its vicinity, and constructing a cDNA library based thereon.

To prove this hypothesis, the present inventor screened a disorder suppressor gene for Alzheimer's disease (AD) as an example of a disorder that accompanies cell death. AD is a neurodegenerative disorder for which no effective therapy has so far been established. AD is clinically characterized by progressive amnesia and dysgnosia, and pathologically by extensive neuronal loss, intraneuronal tangles, and extracellular senile plaques containing a congophylic dense core. So far, four different kinds of mutant genes that cause the early-onset familial AD (FAD): V642I/F/G APP (the numbering is for APP$_{695}$, 695 amino acid version of APP), K595N/M596L APP (NL-APP), presenilin (PS)-1 mutants, and PS-2 mutants (Shastry, B. S. and Giblin, F. J. (1999) Brain Res. Bull. 48, 121-127) have been reported. Expression of these mutant genes induces cell death in nerve cell lines or primary cultured neurons (Yamatsuji, T. et al., (1996) Science 272, 1349-1352; Zhao, B. et al. (1997) J. Neurosci. Res. 47, 253-263; Luo, J. J. et al. (1999) J. Neurosci. Res. 55, 629-642; Wolozin, B. et al. (1996) Science 274, 1710-1713; Wolozin, B. et al. (1998) Neurobiol. Aging 19, S23-27; Guo, Q. et al, (1996) Neuroreport 8, 379-383; Zhang, Z. et al. (1998) Nature 395, 698-702; Guo, Q. et al. (1999) Proc. Natl. Acad. Sci. USA 96, 4125-4130). As it has been generally accepted that progressive neuronal death accounts for most of the clinical symptoms of Alzheimer's disease, the elucidation of the pathological mechanism that causes neuronal death in AD, and the prevention thereof, are mandatory to establish an effective AD therapy that has so far been unavailable.

The present inventor has hitherto established a nerve cell line (F11/EcR/V642I) that inducibly expresses familial Alzheimer's disease mutant V642I amyloid precursor protein (V642I APP) (cf. International Patent Publication No: WO00/14204). In this cell line, V642I APP is expressed in F11 neurons in response to ecdysone treatment. Cell death occurred in almost all the F11/EcR/V642I cells during incubation with ecdysone for 2-3 days, while it scarcely occurred in cells of the control incubation in which V642I APP expression is not induced. The present inventor used these F11/EcR/V642I cells in the screening for a gene that acts as an antagonist against neuronal death induced by V642I APP.

First, poly(A)$^+$RNA was prepared from the occipital lobe derived from a patient diagnosed with sporadic Alzheimer's disease. In Alzheimer's disease, where the principal site of neuronal death is the cerebrum, the neurons of the occipital lobe are hardly damaged. After the reverse transcription of poly(A)$^+$RNA to cDNA, it was incorporated into an expression vector to construct a cDNA library, which was transfected to the above-described F11/EcR/V642I cells to induce the expression of V642I APP upon treatment with ecdysone. After 72 h, plasmids were recovered from cells surviving neuronal death. As a result of repeating the screening procedure using this death-trap method, the present inventor succeeded in identifying a plurality of genes capable of preventing V642I APP-inducible neuronal death.

It was revealed that humanin (HN) cDNA, one of the genes thus isolated encodes a novel polypeptide comprising 24 amino acid residues, which is capable of suppressing AD-associated neuronal death, that is, neuronal death inducible by all kinds of known early-onset familial AD-associated genes (V642I APP, K595N/M596L APP, M146L presenilin (PS)-1 and N141I PS-2) and Aβ1-43. It was found that HN mRNA was produced in the central nervous system as well as in several other organs. It was also revealed that, upon transfection of neurons with HN cDNA, peptide thus produced is secreted into the culture medium. This culture supernatant contained a sufficient amount of activity to significantly protect neurons from the V642I APP-induced death. A synthetic HN polypeptide also showed a neuron-protecting activity against the four different types of AD-associated genes in a similar dose-dependent manner.

Thus, the present inventor has proved that, by screening samples derived from patients suffering from a disorder that accompanies cell death, suppressor genes for the disorder can be obtained. This screening method performed by the present inventor is applicable to not only AD, but also all disorders that accompany cell death as a part of its clinical symptoms.

That is, the present invention enables highly efficient screening of suppressor genes against a variety of disorders that accompany cell death. Moreover, similar to when screening disorder suppressor genes, by using samples containing polypeptides derived from patients suffering from a disorder that accompanies cell death, it is also possible to screen disorder suppressor polypeptides. The present inventor also tested suppressive effects on a disorder that accompanies cell death using nucleic acids derived from patients suffering from the disorder and polypeptides encoded by the nucleic acids, as well as variants thereof. Similar tests are applicable to samples derived from patients suffering from other disorders that accompany cell death, thereby enabling the examination of disorder-suppressive effects. Genes and polypeptides thus obtained by screening and testing can be used not only in the treatment of the disorder, but also as target molecules in the development of novel drugs. The present invention relates to a method of screening for a disorder suppressor gene or polypeptide, and a method for testing a disorder suppressor gene or polypeptide, which are characterized by screening nucleic acids or polypeptides derived from organisms suffering from a disorder that accompanies cell death, and more specifically relates to:

(1) a method of screening for a disorder suppressor gene or a disorder suppressor polypeptide, comprising screening for a nucleic acid or a polypeptide derived from a cell of an organism suffering from a disorder that accompanies cell death, wherein said cell is derived from an area affected by the disorder or from the vicinity of the affected area;

(2) a method of screening for a disorder suppressor gene, wherein said method comprises the steps of:
  (a) expressing in a cell a nucleic acid derived from a cell of an organism suffering from a disorder that accompanies cell death, wherein said cell is derived from an area affected by the disorder or from the vicinity of the affected area;
  (b) detecting in the cell a suppressive effect on the disorder due to the expression of the nucleic acid; and
  (c) selecting the nucleic acid having the suppressive effect;

(3) a method of screening for a disorder suppressor polypeptide or a disorder suppressor gene encoding said polypeptide, wherein said method comprises the steps of:
  (a) administering to a cell (i) a polypeptide derived from a cell of an organism suffering from a disorder that accompanies cell death, or (ii) a polypeptide encoded by a nucleic acid derived from said cell, wherein said cell is derived from an area affected by the disorder or from the vicinity of the affected area;
  (b) detecting in the cell a suppressive effect on the disorder due to the expression of the nucleic acid; and
  (c) selecting the nucleic acid having the suppressive effect;

(4) the method according to any one of (2) or (3), comprising the inducing the cell death associated with said disorder before, or after step (a), and detecting the suppressive effect on the disorder in step (b) using the suppression of cell death as an index;

(5) a method according to any one of (1) to (4), wherein said disorder is a disorder of the cranial nervous system;

(6) the method according to (5), wherein said disorder of the cranial nervous system is Alzheimer's disease;

(7) a method according to any one of (1) to (6), wherein said nucleic acid or polypeptide is derived from the nerve or brain;

(8) a method for testing a suppressive effect on a disorder, wherein said method comprises the steps of:
  (a) expressing in a cell a nucleic acid derived from a cell of an organism suffering from a disorder that accompanies cell death, wherein said cell is derived from an area affected by the disorder or from the vicinity of the affected area; and (b) detecting in the cell the suppressive effect on the disorder due to the expression of the nucleic acid;

(9) a method for testing a suppressive effect on a disorder, wherein said method comprises the steps of:

(a) administering to a cell (i) a polypeptide derived from a cell of an organism suffering from a disorder that accompanies cell death, or (ii) a polypeptide encoded by a nucleic acid derived from said cell, wherein said cell is derived from an area affected by the disorder or from the vicinity of the affected area; and (b) detecting in the cell the suppressive effect on the disorder due to the administration of the polypeptide;

(10) the method according to (8) or (9), comprising the inducing the cell death associated with said disorder before, or after step (a), and detecting the suppressive effect on the disorder in the step (b) using the suppression of cell death as an index;

(11) a method according to any one of (8) to (10), wherein said disorder is a disorder of the cranial nervous system;

(12) the method according to 11, wherein said disorder of the cranial nervous system is Alzheimer's disease; and

(13) a method according to any one of (8) to (12), wherein said nucleic acid or polypeptide is derived from the nerve or brain.

The present invention provides a method for screening disorder suppressor genes or disorder suppressor polypeptides, comprising screening nucleic acids or polypeptides derived from an organism suffering from a disorder that accompanies cell death. Furthermore, this invention provides a method for testing suppressive effects on a disorder using nucleic acids or polypeptides derived from an organism suffering from the disorder. There is no limitation on the type of disorder to which the screening or testing method of this invention is applicable, as long as these disorders accompany cell death. Such disorders include those causing apoptosis and/or necrosis as well as those accompanying cell degeneration.

"Organism suffering from a disorder" includes organisms who show symptoms and also those who have not yet developed visible clinical symptoms but carry factors (or elements) that cause the disorder. In the present invention, for example, organisms having a mutation in a causative gene of a disorder, or aberration in its expression are included in "organism suffering from a disorder". Moreover, animal models, and so on in which clinical symptoms have been artificially reproduced are also included. Such model organisms can be produced by administering factors causing a disorder of interest or by manipulating a causative gene, etc. "Organisms" in this invention include whole organisms, and cultured organs and tissues isolated from organisms. These organisms may be genetically modified. In addition, organs and tissues may be those transplanted to another individual.

Disorders for which the method of this invention is applicable are all disorders that accompany cell death as the main or a part of the pathological features of the diseases. More specifically, for example, in neuronal disorders, included are all the neurodegenerative disorders, encephalitis or encephalopathy caused by exogenous factors such as viruses including HIV, encephalitis due to endogenous factors such as the autoimmune mechanism. Targeted Neurodegenerative disorders may be further classified into two categories: in one category, neurodegeneration occurs in neurons in a specific region, while in the other, it occurs in neurons in an extensive region. For example, Parkinson's disease is caused by neuronal death in the substantia nigra of cerebral basal ganglia, so it is a neurodegenerative disorder belonging to the former category. Additional examples of this category are Huntington's disease in which neuronal death occurs in putamen and corpus striatum of cerebral basal ganglia, retinitis pigmentosa accompanied with death of the retinal neurons, amyotrophic lateral sclerosis caused by death of spinal neurons, and spinocerebellar degeneration accompanied with death of cerebellar neurons. Neurodegenerative disorders belonging to the latter category is represented by Alzheimer's disease, further including dementia with diffuse Lewy bodies, Pick's disease, or anterior temporal dementia, and, alcoholic encephalopathy. Non-neurodegenerative disorders are represented by interstitial pneumonia with death of alveolar epithelial cells as its pathological feature, or fibroid lung, liver cirrhosis caused by death of hepatic parenchymal cells, and so on, also including nephrosclerosis, hypothyroidism, arterosclerosis, and so on.

Thus, although there is no particular limitation in the type of disorders for which the method of this invention is applied, as long as they are disorders accompanying cell death. The instant method is preferably used in searching for suppressor genes or suppressor polypeptides associated with cranial nervous system disorders in particular. Disorders in the cranial nervous system mean those causing injuries in the brain and/or neuronal system. A typical example is the above-described Alzheimer's disease. Research conducted so far have proved that neuronal death occurs in Alzheimer's disease (I. Nishimoto, et al., 1997, Adv. Pharmacol., 41: 337-368). It has been suggested that activation of certain types of APP (I. Nishimoto, et al., 1998, Neurobiol. Aging., 19: S33-S38) and presenilin (Nishimura, et al., 1999, Clin. Genet. 55: 219-225) are involved in these cell deaths. Involvement of ApoE has been also indicated (Namba, Y. et al., Brain Res. 541:163-166 (1991); Saunders, A. M. et al., Neurology 43: 1467-1472 (1993); Corder, E. H. et al., Science 261: 921-923 (1993); Ueki, A. et al., Neurosci. Lett. 163: 166-168 (1993); Sorbi, S. et al., Ann. Neurol. 38: 124-127 (1995); Isoe, K. et. al., Acta Neurol. Scand. 94:326-328 (1996)). Therefore, the method of this invention is preferably used in screening or testing of a disorder suppressor gene or disorder suppressor polypeptide for Alzheimer's disease. The method of this invention may be applied to both sporadic and familial Alzheimer's diseases.

Other than Alzheimer's disease, the method of this invention can also be used to screen or test genes or polypeptides that suppress cranial nervous system disorders caused by neuronal death, for example, for disorders caused by cerebral ischemia (may overlap with the above diseases) (T. Kirino, 1982, Brain Res., 239: 57-69). Furthermore, the method of this invention can be applied also for the screening or testing of suppressor genes and suppressor polypeptides for other neurodegenerative disorders (Helisalmi, S. et al., Neurosci. Lett. 205: 61-64 (1996)) such as Parkinson's disease with dementia (M. H. Polymeropoulos et al., 1997, Science, 276: 2045-2047), dementia with diffuse Lewy bodies (M. G. Spillantini et al., 1998, Proc. Natl. Acad. Sci. USA, 95:6469-6473), frontal dementia, etc.; non-AD type dementia (Helisalmi, S. et al., Neurosci. Lett. 205: 61-64 (1996); Ji, Y. et al., Dement. Geriatr. Cogn. Disord. 9: 243-245 (1998)) such as vascular dementia, dementia accompanying ischemic cerebrovascular disease, a type of alcoholic dementia (Muramatsu, T. et al., J. Neural. Transm. 104: 913-920 (1997)), dementia accompanying Down's syndrome, aging-associated hypomnesia (Blesa, R. et al., Ann. Neurol. 39: 548-551 (1996)), etc.

In the area affected by a disorder that accompanies cell death, and in the vicinity of the affected area, tissues and cells highly susceptible to the disorder are destroyed due to cell death, leaving cells more resistant to the disorder behind. Therefore, suppressor genes or suppressor polypeptides for the disorders can be isolated highly efficiently from samples collected from the affected area or its vicinity in such an organism. "the affected area or its vicinity" means the area or its vicinity showing disorder-associated alterations or clinical symptoms, and may also contain normal cells. For example, when the affected area is localized within an organ, the organ as a whole may be referred to as a vicinity of the affected area. In the case of cerebral disorders where cell degeneration is observed, for example, in the frontal lobe, the brain as a whole including the occipital lobe is included in "the affected area or its vicinity."

There is no particular limitation in organs from which tissues of the affected area or its vicinity are collected, and any organ or tissue showing cell death as a clinical symptom of the disorder (for example, neuronal tissues in the case of neuronal disorders, lung tissues in the case of lung disorders) may be used. If a cDNA library is prepared from these tissues and cells, that library has condensed mRNA expressed in cells that have survived in the affected tissue. Furthermore, polypeptides of interest can be extracted according to standard methods known in the art from the tissues and cells.

When a difference in the clinical symptoms is observed in an affected area or its vicinity, samples are preferably prepared from tissues or cells that are as near to the affected area as possible, and those that have slight clinical symptoms. It is also preferable to prepare samples from tissues or cells collected from the normal or nearly normal parts present in the affected organ, independent of the affected area. Such cells may be high in the expression level of disorder suppressor genes compared to other cells, so a highly efficient screening of disorder suppressor genes or polypeptides can be done. Slight clinical symptoms means that, in a disordered organism, the level of symptoms in a particular area is slight compared to the most severely affected area. When multiple symptoms are seen in association with the disorder, at least any one of them may be compared. For example, in organs or tissues showing cell death as a pathological feature of a disorder, RNA is extracted from areas in which cells efficiently survive. For example, when a severe symptom is observed in the cranial frontal cortex while the symptom in the occipital cortex or cerebellum is relatively slight, samples can be prepared from the latter tissues. In the example of this invention, for example, cDNA library has been constructed from occipital lobe where there is practically no neuronal damage within the cerebrum, a principal site of neuronal death in AD. Similarly, in other disorders, RNA can be extracted from cells in the affected area or its vicinity to construct cDNA library.

Preparation of nucleic acids or polypeptides from tissues or cells can be performed according to the method well known in the art (Sambrook, J. et al., Molecular Cloning, 2nd ed., Cold Spring Harbor Lab. press, 1989). In the present invention, "polypeptides derived from cells of an organism" include cell lysates or cell extracts, fractions thereof, crude or purified polypeptides, etc. Cell extracts may be appropriately fractionated using a suitable fractionation method. Such methods well known in the art for fractionating or purifying proteins, include ammonium sulfate precipitation, cationic or anionic exchange chromatography, gel filtration, affinity chromatography, HPLC etc. Herein, polypeptides may be free or bound to a carrier. In this invention, "polypeptides" mean peptides or proteins comprising two or more amino acid residues linked each other. Polypeptides also include short-chained ones usually called peptides, oligopeptides or oligomers. Polypeptides are not limited to those having relatively short chains, and include those having long chains such as those called proteins. They may be polypeptides comprising, for example, 300 amino acid residues or more, 500 amino acid residues or more, or 1000 amino acid residues or more. That is, polypeptides as used herein include proteins.

Furthermore, in the present invention, "nucleic acids derived from cells in organisms" include nucleic acids obtained from organisms and those synthesized from the nucleic acids, nucleic acids comprising those, and amplified products thereof. Nucleic acids include both DNA and RNA, comprising, for example, DNAs prepared from organisms (e.g. chromosomal DNA or organelle DNA, etc.), transcriptional products thereof, RNAs prepared from organisms, cDNAs synthesized from the RNAs, fragments thereof, etc. In addition, "nucleic acids derived from organisms" include vectors containing these nucleic acids, and amplified products of the vectors. Preferably, mRNA prepared from cells is reversely transcribed to synthesize cDNA, which is inserted into an expression vector to construct the expression cDNA library. Synthesis of cDNA by the reverse transcription of RNA and preparation of an expression library from cDNA can be carried out according to the method well known in the art (Sambrook, J. et al., Molecular Cloning, 2nd ed., Cold Spring Harbor Lab. press, 1989). Examples of vectors used in the construction of an expression library are plasmid vectors (e.g. pcDNA, pEF-BOS, etc.) and viral vectors, etc.

Screening of disorder suppressor genes or polypeptides are carried out by screening nucleic acids or polypeptides thus prepared. Herein, screening of nucleic acids means identification or selection of candidate nucleic acids or fractions containing the same from nucleic acid samples or fractions containing the nucleic acids. Moreover, according to the present invention, it is also possible to test suppressive effects on disorders utilizing these nucleic acids or polypeptides.

For the extraction of RNA from tissues, in order to suppress RNA degradation, it is necessary to collect a sample and prepare nucleic acid as rapidly as possible. In the method of this invention, nucleic acids may be simply prepared directly from cells in the affected area or its vicinity in an organism suffering from a disease, so that separation of specific cells from tissues by tissue staining and cell sorting is not required. Therefore, suitable tissue can be immediately collected from such an organism so as to minimize nucleic acid degradation.

Nucleic acids or polypeptides used in the screening or testing method of this invention may be combined with solvents or solutes to form compositions. For example, they may be appropriately dissolved in sterilized water, buffers, physiological saline, mediums, serum, or solvents having combinations thereof. In these solutions a salt, protein, surfactant, preservative, and so on may be also dissolved, if necessary. In addition, nucleic acids can be combined with various transfection reagents such as LipofectAMINE (GIBCO BRL) when transferred into cells.

The screening method of the present invention is characterized by the use of nucleic acids or polypeptides derived from cells in an area affected by a disorder that accompanies cell death, or in the vicinity of the affected area, of an organism suffering from the disorder. It is expected that a library having condensed disorder suppressor genes can be constructed by preparing RNAs expressed in cells in the affected area, or in its vicinity. Similarly, a library having condensed disorder suppressor polypeptides may also be constructed by preparing polypeptides expressed in cells in the affected area or its vicinity. Libraries thus constructed are applicable to the functional screening and other various screenings aimed at screening disorder suppressor genes or polypeptides. For example, when a gene or protein causing a disorder has been identified, the above-described library may be used to screen a disorder suppressor gene or polypeptide that functions to normalize the expression and activity of the causative gene or protein as much as possible. For example, when a therapeutic effect can be expected by controlling the biochemical function of a causative protein of a disorder, it is effective to screen a library in which disorder suppressor genes or polypeptides are thought to be condensed using the method of this invention and this biochemical function as an index. These screenings can be carried out utilizing well-known systems used in the analysis of a pathological feature of a disorder and functional analysis of a causative gene of a disorder. Nucleic acids prepared from the affected area and its vicinity are appropriately incorporated into an expression vector and transferred to cells to detect their actions.

Screening of the present invention can be performed, for example, by detecting suppressive effects of test nucleic acids or polypeptides on a disorder. This screening method is a method that screens suppressor genes or polypeptides using their suppressive effect as an index, without focusing on the biochemical activity of the causative genes of the disorder. One of the screening methods comprises the following steps of:

(a) expressing in a cell a nucleic acid derived from a cell of an organism suffering from a disorder that accompanies cell death, wherein said cell is derived from an area affected by the disorder or from the vicinity of the affected area;

(b) detecting in the cell a suppressive effect on the disorder due to the expression of the nucleic acid; and (c) selecting the nucleic acid having the suppressive effect.

Alternatively, by a method comprising the following steps of:

(a) administering to a cell (i) a polypeptide derived from a cell of an organism suffering from a disorder that accompanies cell death, or (ii) a polypeptide encoded by a nucleic acid derived from said cell, wherein said cell is derived from an area affected by the disorder or from the vicinity of the affected area;

(b) detecting in the cell a suppressive effect on the disorder due to the expression of the nucleic acid; and (c) selecting the nucleic acid having the suppressive effect.

Furthermore, by similar processes as those described above, it is possible to examine suppressive effect of a test polypeptide and test nucleic acid, or a polypeptide encoded by said nucleic acid on disorder.

One of the testing methods comprises the following steps of:

(a) expressing in a cell a nucleic acid derived from a cell of an organism suffering from a disorder that accompanies cell death, wherein said cell is derived from an area affected by the disorder or from the vicinity of the affected area; and (b) detecting in the cell the suppressive effect on the disorder due to the expression of the nucleic acid.

Alternatively, one of the testing methods can be performed by a method comprising the following steps of:

(a) administering to a cell (i) a polypeptide derived from a cell of an organism suffering from a disorder that accompanies cell death, or (ii) a polypeptide encoded by a nucleic acid derived from said cell, wherein said cell is derived from an area affected by the disorder or from the vicinity of the affected area; and (b) detecting in the cell the suppressive effect on the disorder due to the administration of the polypeptide.

Testing of a disorder suppressive effect can be performed by assessing any of the target symptoms of the disorder and examining whether this symptom is suppressed by the expression of a test nucleic acid or administration of a test polypeptide. The assessed symptom may be either macroscopic or microscopic. For example, as a microscopic symptom, phenotype changes of cells and changes in the expression level disorder-associated genes that occur in relation to a disorder can be also used as indexes of suppressive effects.

In the above-described screening or testing, there is no particular limitation on the type of host cells used for expression of nucleic acids or administration of polypeptides, for example, mammalian cells can be used. There is no limitation on the type of mammalian cells, and non-human mammalian cells from mice, rats, rabbits, monkeys, and so on, as well as human cells can be used. Examples of mammalian cell lines used in general are CHO cell, COS cell, NIH3T3 cell, HEK293 cell, and so on. A cell line derived from tissue equal to the one affected tissue by the target disorder may be used. For screening or testing suppressor genes or polypeptides for the cranial nervous system disorders, neurons are preferably used. Neurons include, for example, cells in the nervous system, cells derived from cells in the nervous system, nerve precursor cells, and so on also including neuroblastoma, pheochromocytoma, teratoma, fusion cells formed using cells in the nervous system, fetal germinal cells, and so on. Examples of nerve cell lines usable in the method of this invention are F11 cells (D. Platika, et al., 1985, Proc. Natl. Acad. Sci. USA, 82: 3499; T. Yamatsuji, et al., 1996, Science, 272: 1349), SH-SY5Y cells (L. Odelstad et al., 1981, Brain Res., 224: 69-82), PC12 cells (L. A. Greene and A. S. Tischler, 1976, Proc. Natl. Acad. Sci. USA, 73: 2424-2428), NTERA2 cells (J. Skowronski and M. F. Singer, 1985, Proc. Natl. Acad. Sci. USA, 82: 6050-6054), P19 cells, and cells derived from these cells. As to NTERA2 cells and P19 cells, in particular, cells in which nerve differentiation has been induced by treatment with retionoic acid are preferably used. Examples of cells derived from F11 cells are F11/EcR cells (Y. Hashimoto et al., J. Biol. Chem. published on-line on Aug. 3, 2000), F11/EcR/V642I cells (T. Niikura et al., 2000, Biochem. Biophys. Res. Commun. 273: 442-447) (both, cf. examples). Primary neuronal cultures (for example, primary culture of the rat cerebral cortex) can be also used. Cellular expression of a nucleic acid can be performed by incorporating the nucleic acid into an expression vector and transferring the transformed vector into host cells. Administration of a polypeptide can be carried out by its adding it to the culture medium or injecting it into cells. Cells may be those within an individual. Expression of a nucleic acid in an individual may be carried out by administration of an expression vector containing the nucleic acid to the individual. As an expression vector, for example, viral vector can be used. As a viral vector, the well-known vector systems such as adenoviral vectors, retroviral vectors, etc can be utilized. Administration of polypeptides can be performed, besides the direct administration thereof into tissues or cells, through well known routes such as intravenous, oral, intramuscular, subcutaneous and intraperitoneal administrations. Examples of organisms used in the screening or testing are non-human mammals such as mice, rats, rabbits, monkeys, etc. More specifically, a variety of disorder models constructed in vivo or in vitro may be applied to the method of the present invention. A number of such disorder models are known in the art.

As a result of detection, when the expression of a test nucleic acid or administration of a test polypeptide acts so as to suppress or normalize the onset, symptoms and/or progress of a disorder, the nucleic acid or polypeptide is assessed to have a suppressive effect on the disorder. Thus, nucleic acids or polypeptides found to have a significant suppressive effect on a disorder are assessed as genes or polypeptides having a suppressive effects on the disorder, respectively. In these tests, more detailed assays of the suppressive effect such as quantification thereof can be performed.

Effects of test nucleic acids or test polypeptides may be direct or indirect. For example, a nucleic acid or its expression product itself (RNA or polypeptide) may have a effect, and a nucleic acid or its expression product may exert effects through acting on a different factor. These nucleic acids that can be isolated or selected by the screening method or testing method described above become disorder suppressor genes. In addition, a polypeptide that can be isolated or selected by the above described screening method or testing method become a disorder suppressor polypeptide. Nucleic acid encoding the isolated polypeptide (disorder suppressor genes) can be obtained, for example, by screening genomic DNA and cDNAs using DNA probes and primers prepared based on the partial amino acid sequences analyzed for the isolated polypeptide.

A screening or testing system for distinguishing disorder suppressive effects by cell death can be also constructed. This screening or testing method is a method performed solely relying on cell death itself, which is a pathological feature of a disorder, as an index. In this screening or testing method, cell death associated with a disorder is induced in the above-described step (a) or before or after the step, and suppressive effect on the disorder is detected in step (b) using the suppression of the cell death as an index. In the following Example, using an Alzheimer's disease (AD)-associated cell death-inducible cell system, the present inventors screened genes suppressing the cell death. In this method, a familial AD mutant amyloid precursor protein (APP) is expressed in neurons, and genes suppressing the cell death induced are screened. Induction of neuronal death is not limited to that by the expression of V642I APP used in the Example, and can be performed by any desired treatment that induces cell death (cf. International Patent Publication No: WO00/14204 and International Patent Application No: PCT/JP00/02830). Furthermore, as described in Examples, polypeptides and genes isolated by the screening, polypeptides encoded by the genes, derivatives thereof, and so on can be examined in detail for their suppressive effects on neuronal death induced by a variety of FAD genes and Aβ.

As an example of a specific method, neurons (for example F11 cells) are transfected with only a vector expressing each of the FAD genes: V642I/F/G APP, NL-APP, M146L PS-1 or N141I PS-2, or together with a vector expressing a nucleic acid to be tested. Alternatively, cell death may be induced by the addition of Aβ (for example, Aβ 1-43) to a primary neuronal culture (for example, a primary culture of rat cerebral cortex). Furthermore, cell death may be induced also by the addition of APP ligand (including APP antibody) or ApoER-1 ligands such as ApoE4. After culturing cells having a test nucleic acid expressed, cell mortality is measured. FAD genes can be conditionally expressed using an inducible promoter. When there is a statistically significant reduction in cell mortality induced under the condition in which a test nucleic acid is expressed compared with that induced under the condition in the absence of the test nucleic acid expression, this nucleic acid is assessed to have the disorder suppressive effect. In the case of using a polypeptide as a test sample, cell death is measured in the presence or absence of a sample containing this polypeptide. When there is a statistically significant reduction in cell death induced in the presence of a tested polypeptide compared with that induced in the absence of the polypeptide, this polypeptide is assessed to have a disorder suppressive effect. In the testing and screening of the action of a nucleic acid, instead of expressing a test nucleic acid, a polypeptide encoded by the nucleic acid to be tested is prepared beforehand, and cell death may be measured in the presence or absence of this polypeptide.

A screening or testing method that uses the suppression of cell death as an index is similarly applicable to disorders other than Alzheimer's disease. Disorder-associated cell death can be induced, for example, by administering a factor that reproduces the disorder of interest or by expressing a causative gene of the disorder. Specifically, for example, a system in which cell death is induced by expressing polyglutamine in neurons can be used (de Cristofaro, T. et al., 2000, Biochem. Biophys. Res. Commun. 272: 816-821). This system has been known as an experimental model of spinocerebellar ataxia (SCA) and Huntington's disease, and is applicable to the testing or screening of suppressor genes and polypeptides for these disorders in the present invention. Another example of an experimental disorder model is a system expressing SOD1 mutants (Silani, V. et al., 2000, J. Neurol. 247 Suppl. 1: 128-136), which has been known as a model of amyotrophic lateral sclerosis (ALS), and screening of suppressor genes and suppressor polypeptides for this disorder also is a application object of the method of this invention. In addition, a system in which neurons are treated with a partial peptide (116-126) of a prion (Thellung, S. et al., 2000, Int. J. Dev. Neurosci. 18: 481-492) is utilizable in this invention as a model of encephalopathy caused by prions. Moreover, a system in which pancreatic β-cells are treated with human amylin (Bai, J. Z. et al., 1999, Biochem. J. 343 Pt 1: 53-61) can be used as a model of Type I diabetes mellitus. Furthermore, a system in which T cells such as Jurkat cells are treated with anti-Fas antibody (Li, X. K. et al., 2000, Biochem. Biophys. Res. Commun. 273: 101-109) can be utilized as a model of fulminant hepatitis, and a system in which T cells are similarly treated with a T cell receptor antibody (Vito, P. et al., 1996, J. Biol. Chem. 271: 31025-31028) can be used as a model of autoimmune disorders. In addition, a system expressing a rhodopsin mutant (Liu, C. et al., 1999, J. Neurosci. 19: 4778-4785) is also an application object of the method in this invention as a model of retinitis pigmentosa. In these models, the detection or screening of this invention can be carried out, for example, by transferring nucleic acids or polypeptides derived from an area affected by a disorder or the vicinity of the affected area of an organism suffering from the disorder, and detecting the cell death therein. There is no limitation on the origin of the nucleic acid or polypeptide specimens, examples being those derived from tissues of patients, disorder model animals, or model culture systems, etc.

In the following Example, the present inventors examined the effect of HN peptide using a system of neuronal death induced by Q79, a polyglutamine with 72 repeats (Example 8). As described above, polyglutamine Q79 is thought to be a causative of Huntington's disease (HD) and certain forms of spinocerebellar ataxia (SCA) (Ikeda, H. et all. (1996) Nat. Genet. 13, 196-202; Kakizuka, A. (1997) Curr. Opin. Neurol. 10, 285-290). Specifically, the present inventors have examined the suppressive effect of HN polypeptide by transfecting F11/EcR cells with an ecdysone-inducible Q79 plasmid (pDN-E/G5H-Q79), and inducing neuronal death in the presence or absence of ecdysone to examine the suppressive effect of HN polypeptide. A system equal to this can be used in the screening and testing of suppressor genes or suppressor polypeptides for Huntington's disease (HD) and spinocerebellar ataxia (SCA). That is, these screenings and testing can be carried out by transfecting the above-described cells with an expression library constructed from mRNA prepared from the area affected by a disorder or the vicinity of the affected area to detect cell death.

Furthermore, the present inventors examined the effect of HN peptide using a system of neuronal death induced by familial amyotrophic lateral sclerosis (familial ALS)-associated Cu/Zn-dependent superoxide dismutase (SOD1) mutants (Example 8). In this experiment, cell death was induced by mutant A4T, G85R, or G93A of SOD1. By applying a similar system as this to the method of this invention, it is possible to perform testing and screening of suppressor genes or polypeptides for ALS. Similarly, screening and testing of this invention may be carried out using other disorder model systems.

Examples of methods for detecting cell death are cell number counting, counting of viable cells by trypan blue exclusion assay, biochemical assay using MTT, etc. Cell death may be detected also by LDH release assay, and also by using a method for detecting apoptosis. Methods for detecting apoptosis are exemplified by the TUNEL method, DNA ladder method, method using an electron microscope, or a method that relies on the detection of unique alterations of nuclei and cytoplasmic membrane, etc. Examples of the last method are those for measuring annexin V, morphological alterations of nuclei or caspase activity.

As a result of detection, when a significant cell mortality-reducing effect is confirmed, test nucleic acids or polypeptides used in screening or testing are assessed to have a suppressive effects on a disorder of interest. In this case, a test nucleic acid or polypeptide need not completely inhibit cell death, but it is assessed to be effective when its capable of significantly reducing the cell mortality compared to when the nucleic acid or polypeptide is absent. Thus, disorder suppressor genes or disorder suppressor polypeptides can be isolated or selected.

Genes and polypeptides isolated or selected by the above-described methods of the present invention are expected to be useful in the prevention and therapy of disorders. Disorder suppressor genes can be amplified and expressed by inserting them into appropriate vectors. Such vectors may be utilized also for the purpose of gene therapy. As vector systems used in gene therapy, adenovirus vectors, AAV (adeno-associated virus) vectors, herpes virus vectors (all of these described in Robbins and Ghivizzani, Pharamacol. Ther. 80: 35-47, 1998), retrovirus vectors (Engel and Kohn, Front. Biosci. 4: e26-33, 1999), lentivirus vectors (Lundstrom, K., 1999, J. Recept. Signal. Transduct. Res. 19: 673-686), and so on may be utilized, but is not limited thereto. Furthermore, so far as the suppressive effect of interest is retained, the base sequence of gene and amino acid sequence of polypeptide may be appropriately modified by a deletion, addition, insertion and/or substitution, and so on, respectively.

When the isolated gene encodes a peptide, the peptide can be produced by expressing the gene in appropriate hosts. There is no particular limitation in the type of hosts used for the production of a polypeptide, and cells such as *E. coli*, yeast, mammalian cells, plant cells, insect cells, or individuals from which these cells are derived may be used. Host-vector systems are exemplified by the baculovirus-Sf cell system (Okamoto, et al., J. Biol. Chem. 270: 4205-4208, 1995), pcDNA-CHO cell system (Takahashi, et al., J. Biol. Chem. 270: 19041-19045, 1995) CMV promoter plasmid-COS cell system (Yamatsuji, et al., EMBO J. 15: 498-509, 1996), and so on, but are not limited thereto.

Moreover, the above-described nucleic acids or polypeptides can be artificially synthesized or modified to form derivatives. Herein, "derivatives" are molecules having the structures altered by a modification, addition, mutation, substitution or deletion of a functional group of a nucleic acid or polypeptide. Such alterations can be performed by methods well known in the art. Modifications of functional groups are carried out aiming at, for example, the protection and stabilization of functional groups in the nucleic acid or polypeptide, or the control of migration to tissue or disorder-suppressing activity of the nucleic acid or polypeptide.

Nucleic acids or polypeptides thus isolated, or polypeptides encoded by the nucleic acids can be made into disorder-suppressing reagents. A nucleic acid can be appropriately incorporated into a vector, and the resulting transformed vector can be used as a reagent. For a reagent comprising a nucleic acid or polypeptide, a nucleic acid or polypeptide can be used by itself, or by appropriately combining with sterilized water, physiological saline, a buffer, salt, stabilizer, preservative, surfactant, another protein (such as BSA) transfection reagent (including lipofection reagent), etc. They may be mixed beforehand, or separately stored until mixed prior to use.

Furthermore, the above-described nucleic acids (or vectors) or polypeptides are used to prepare a pharmaceutical composition for a disorder. As a pharmaceutical composition, a nucleic acid or polypeptide itself may be directly administered to patients, or may be formulated by pharmaceutical preparation methods well known in the art. For example, the composition may be administered after appropriately formulating it with pharmacologically acceptable carriers or medium, specifically, sterilized water or saline, vegetable oils, emulsifiers, suspending agents, detergents, stabilizers, sustained-release preparations, and such. A pharmaceutical composition of this invention may be in the form of an aqueous solution, tablet, capsule, troche, buccal tablet, elixir, suspension, syrup, nasal drop, inhalant solution, and such. The content of the polypeptide in these preparations makes a suitable dosage acquirable.

Administration to patients may be carried out depending on the properties of the used active ingredient. Example of suitable administration methods include percutaneous, intranasal, transbronchial, intramuscular, intraperitoneal, intravenous, intraspinal, intracerebroventricular, or oral administrations, but are not limited thereto. When using the pharmaceutical composition in the treatment of cerebral neurodegenerative diseases, it is preferable to introduce the pharmaceutical composition to the central nervous system by an appropriate arbitrary route including a intravenous, intraspinal, intracerebroventricular, or intradural injection. The dosage varies according to the age, body weight, condition of a patient, method of administration, and such, but one skilled in the art can suitably select them. The dosage and administration method varies depending on the histological localization of the active ingredient of the pharmaceutical composition of the present invention, therapeutic purpose, body weight, age, and condition of a patient, and such, but can be selected suitably by those skilled in the art.

DNA fragments were aligned with respect to the longest sequence (from −934 to 600; the number 1 nucleotide corresponds to the first nucleotide of Humanin ORF, and the nucleotide adjacent to it is numbered −1). Activities of the fragments against F11/EcR cell death induced by V642I APP are indicated under the item "rescue activity". F11/EcR cells were transfected for 3 hours with pIND (1 µg), encoding V642I APP, and 1 µg of either pEF-BOS or pEF-BOS encoding each of the DNA fragments; and then, were treated with ecdysone for 72 hours. Cell death was measured by trypan blue exclusion assay. A DNA fragment was determined to antagonize cell death (described as "Y" under the item "rescue activity") when the mortality of cells transfected with the DNA fragment showed a statistically significant difference with that of cells transfected with pEF-BOS. "N" indicates the absence of such a significant antagonizing activity.

Figure 1:
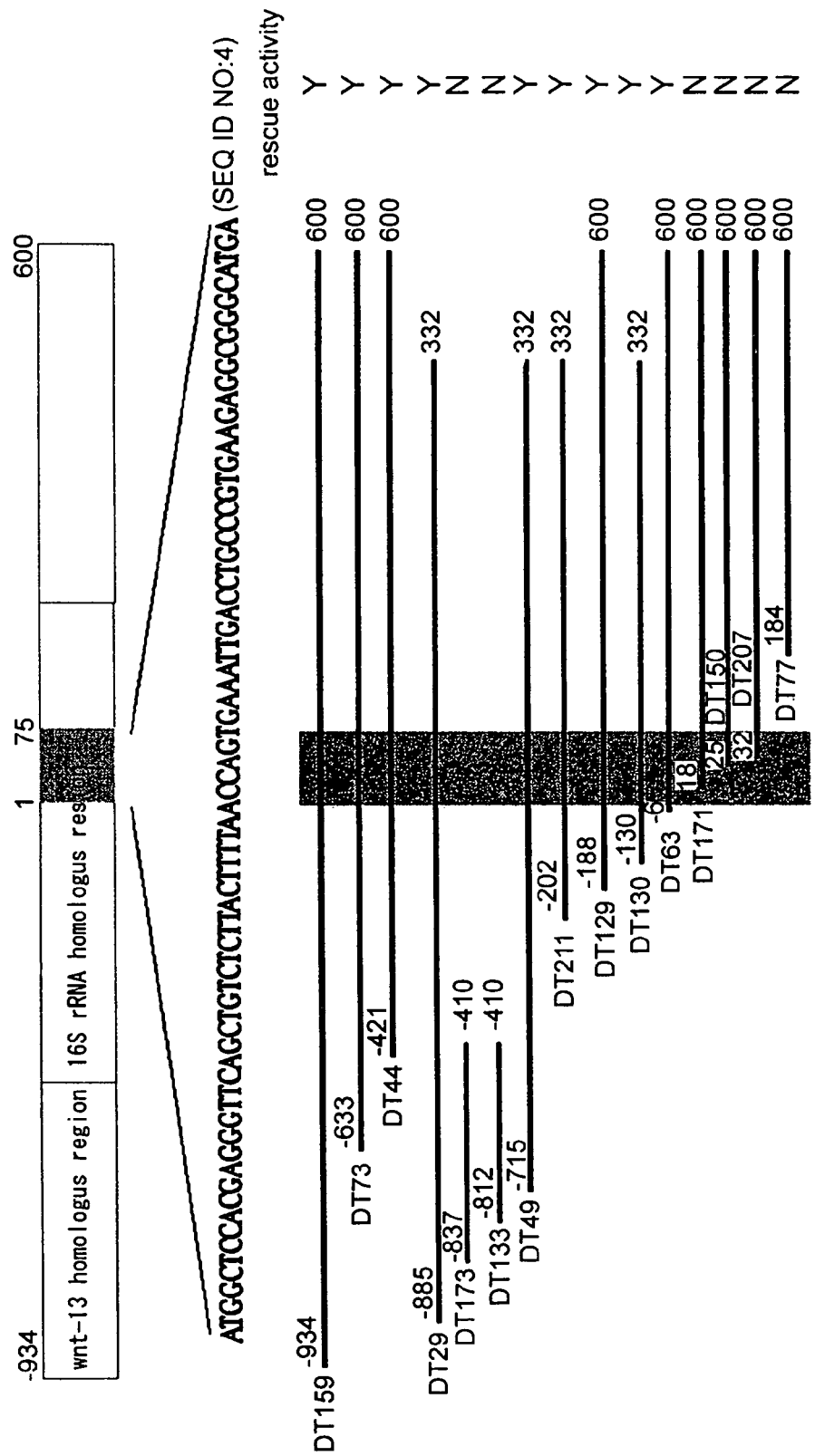
FIG. 1 depicts a schematic illustration of the region in Humanin cDNA clone that encodes a polypeptide that antagonizes cell death caused by V642I APP.
Figure 2:
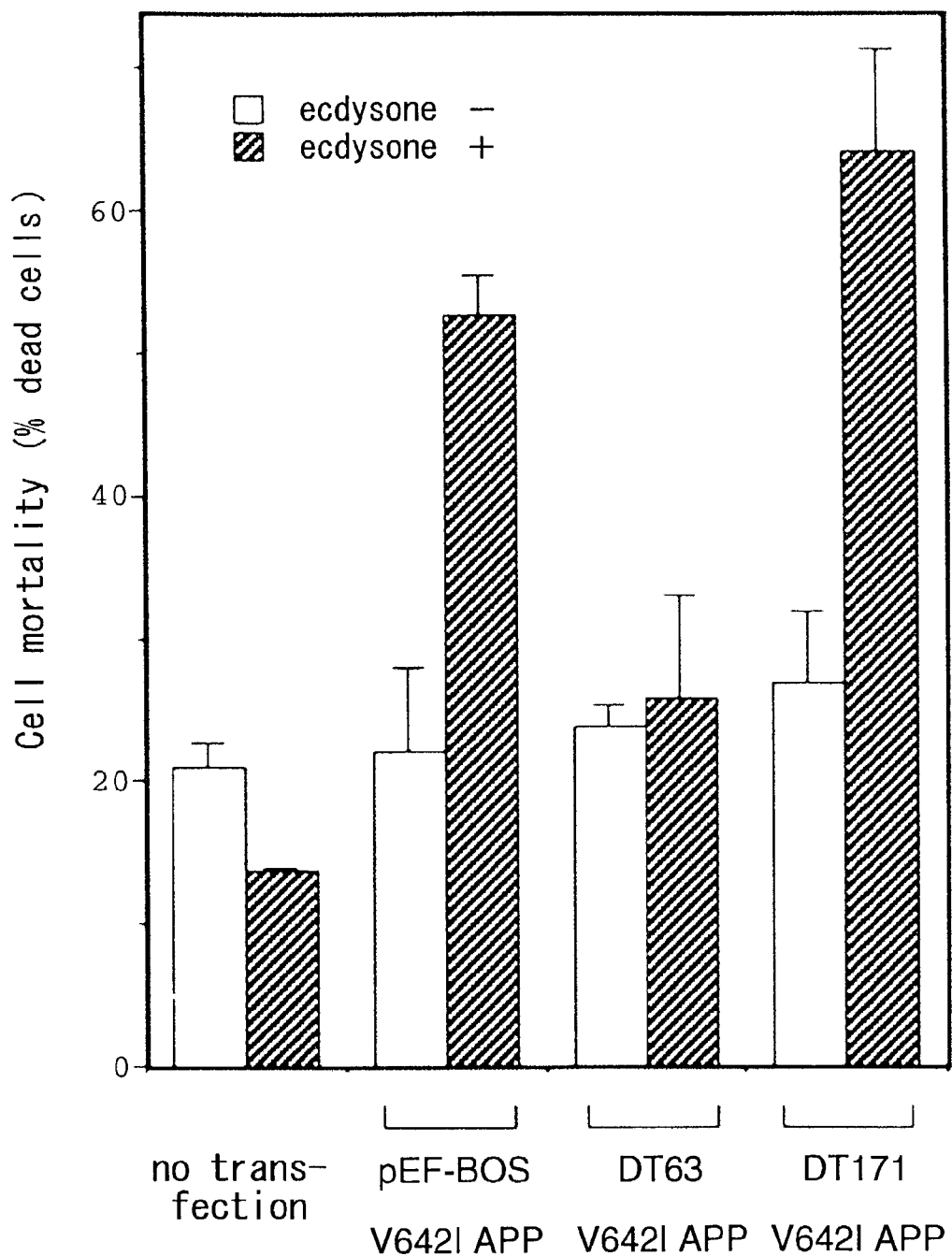

FIG. 2 depicts a graph demonstrating the effects of DT63 clone and DT171 clone on neuronal death caused by ecdysone-induced expression of V642I APP. F11/EcR cells were transfected with ecdysone-inducible V642I APP plasmid, and any one of pEF-BOS, DT63, or DT171 (DT63 and DT171 were cloned in pEF-BOS), and were treated with Ponasterone (ecdysone). A group without ecdysone treatment was also set up. 72 hours after ecdysone treatment, cell death was measured by trypan blue exclusion assay. Cell death of the group without ecdysone treatment was measured similarly. The values with error bars in the graph represent mean ±S.D. values of three independent transfection experiments. DT63 and DT171 are shown in FIG. 1.

Figure 3:
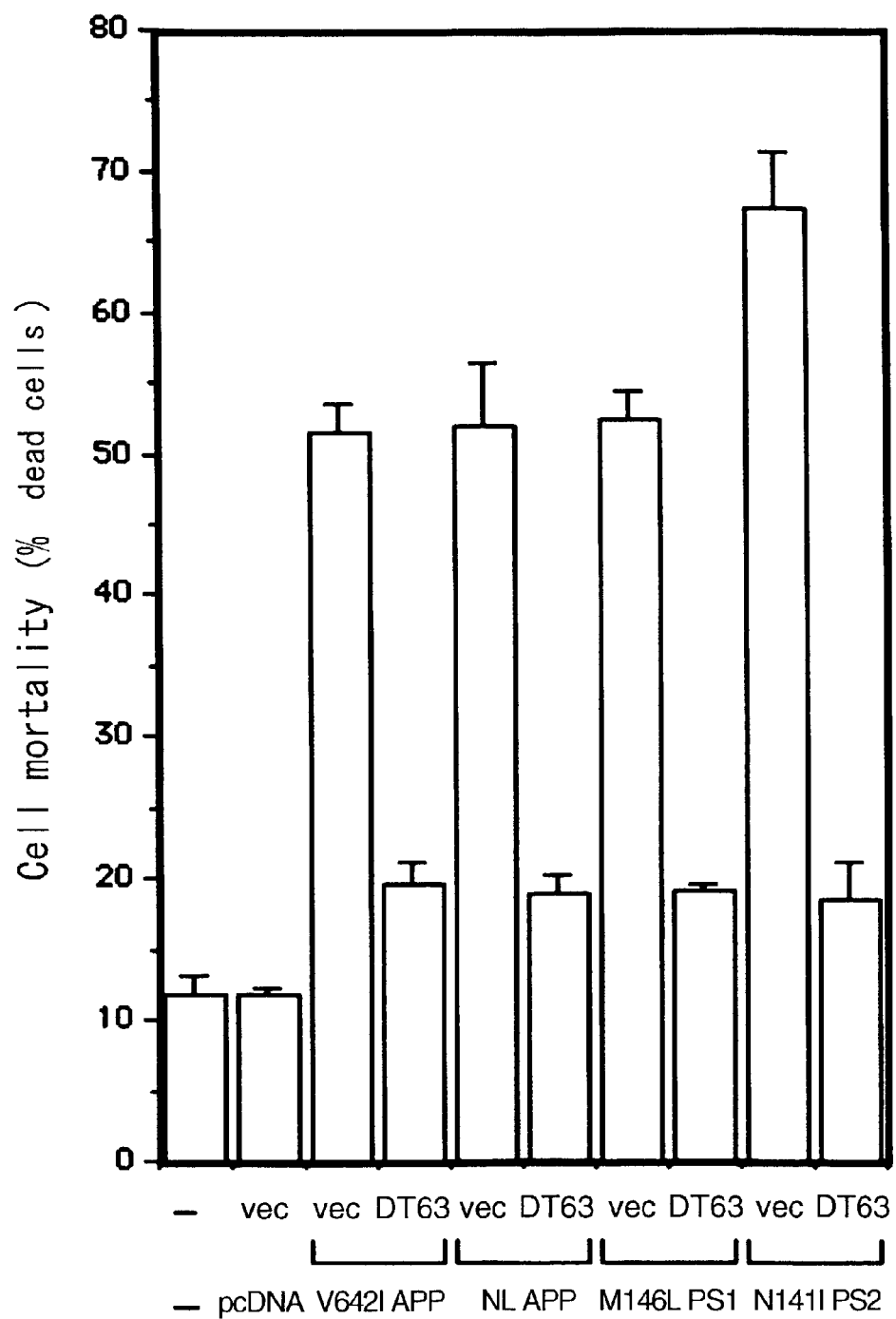

FIG. 3 depicts a graph demonstrating the effect of DT63 clone on neuronal death induced by the expression of the FAD gene. F11 cells were transfected with pcDNA; or pcDNA encoding V642I APP, NL-APP, M146L PS-1, or N141I PS-2; and pEF-BOS (vec); or pEF-BOS encoding DT63; and were cultured for 72 hours. Cell death was measured by trypan blue exclusion assay. The values with error bars in the graph indicate the mean ±S.D. values of three independent transfection experiments.

Figure 4:
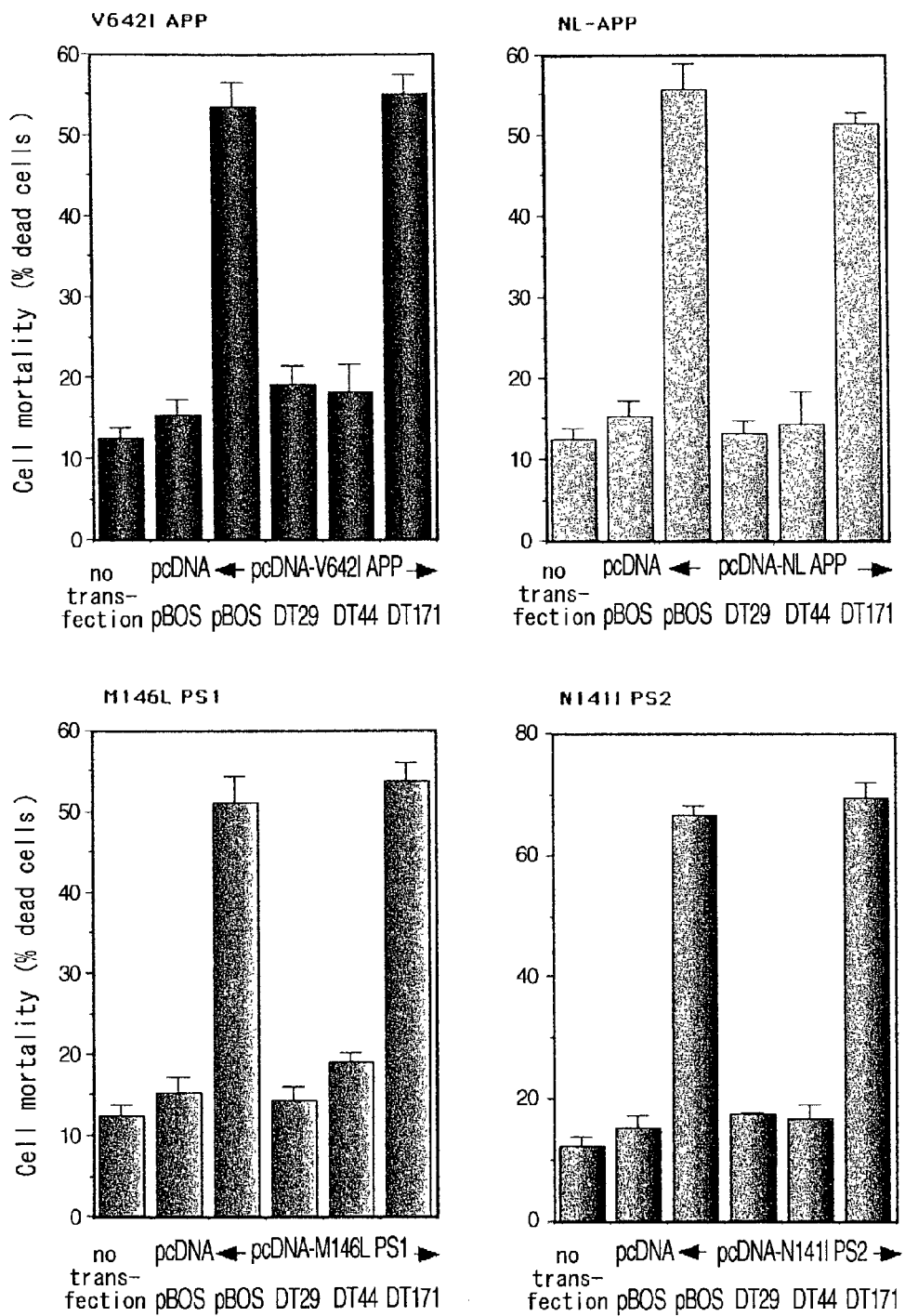

FIG. 4 depicts graphs indicating the effects of DT29, DT44, and DT171 clones on F11 cell death caused by FAD gene transfection. Similarly to FIG. 3, F11 cells were transfected with pcDNA; or pcDNA encoding either V642I APP, NL-APP, M146L PS-1, or N141I PS-2; and pEF-BOS (pBOS); or pEF-BOS encoding DT clone; and were cultured for 72 hours. Cell death was measured by trypan blue exclusion assay. DT29 and DT44 are shown in FIG. 1. Basal cell mortality (no transfection, pcDNA+ pBOS) was concordant in the three experiments performed simultaneously. Similar experiments were performed at least three times. The values with error bars in the graph indicate the mean ±S.D values.

Figure 5:
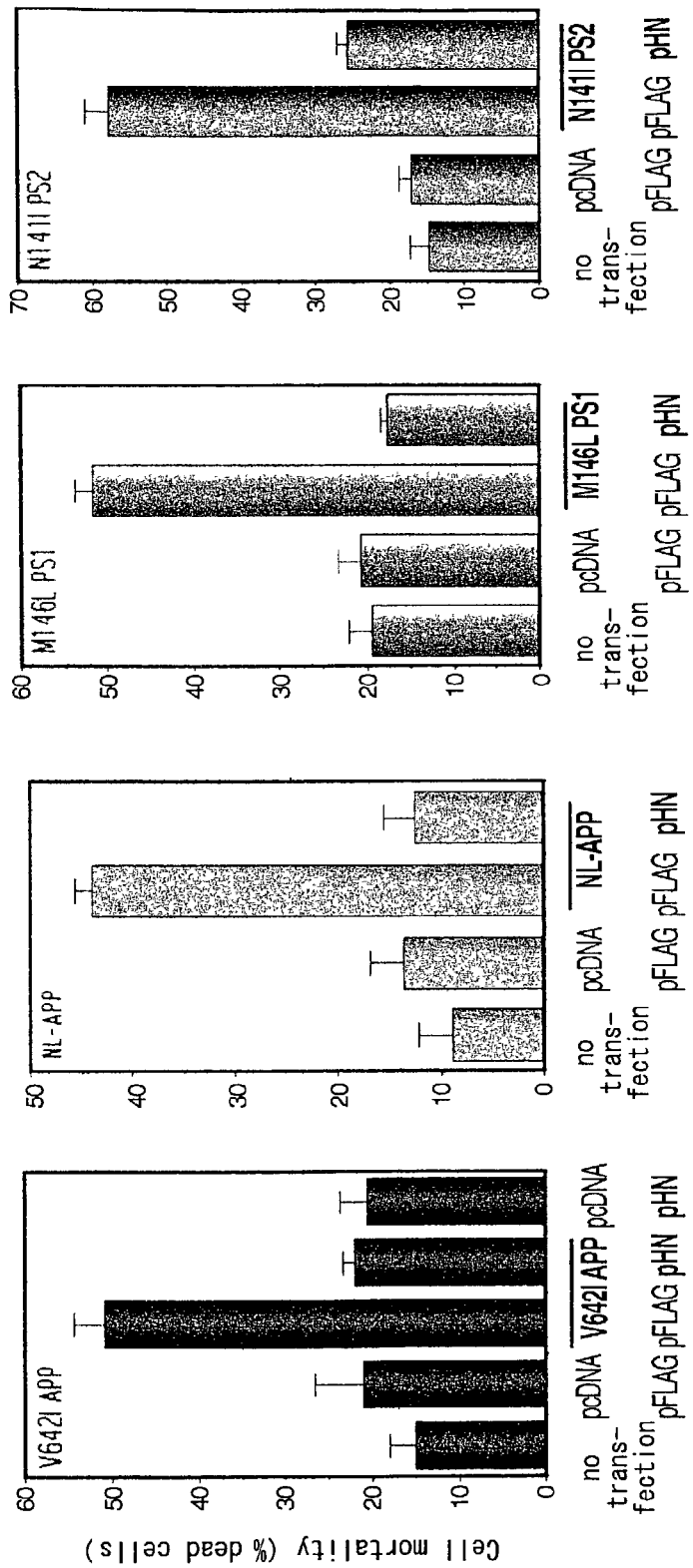

FIG. 5 depicts graphs demonstrating the effect of Humanin-encoding plasmid pHN on neuronal death induced by expression of a FAD gene. F11 cells were transfected with an empty vector (pcDNA); or pcDNA encoding V642I APP, NL-APP, M146L PS-1, or N141I PS-2; and PFLAG; or pFLAG encoding HN (pHN); and were cultured for 72 hours. Cell death was measured by trypan blue exclusion assay. The values are mean ±S.D. values obtained by three independent experiments.

Figure 6:
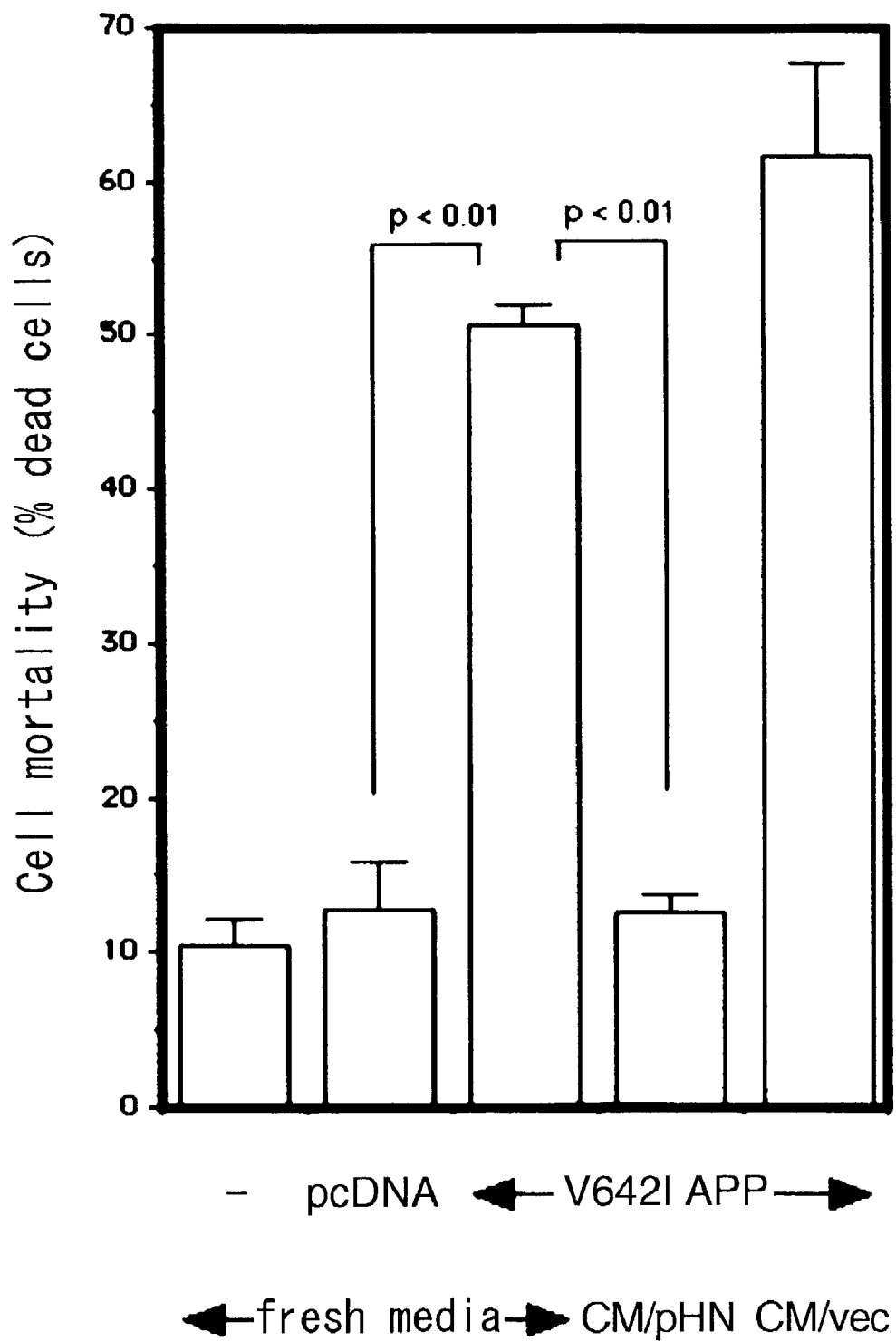

FIG. 6 depicts a graph demonstrating the suppressive effect of a culture supernatant from pHN-transfected F11 cells on neuronal death induced by V642I APP. F11 cells were transfected for 3 hours with either pcDNA or pcDNA encoding V642I APP, in the absence of serum; cultured in HamF-12 containing 18% FBS for 2 hours; and cultured in CM/F11-pHN (CM/pHN), CM/F11-vec (CM/vec), or fresh media (fresh HamF-12 containing 18% FBS) for 67 hours. 72 hours after the transfection, cell death was measured by trypan blue exclusion assay. The values are indicated as mean ±S.D. values of three independent experiments. p<0.01; according to a Student's t test.

Figure 7:
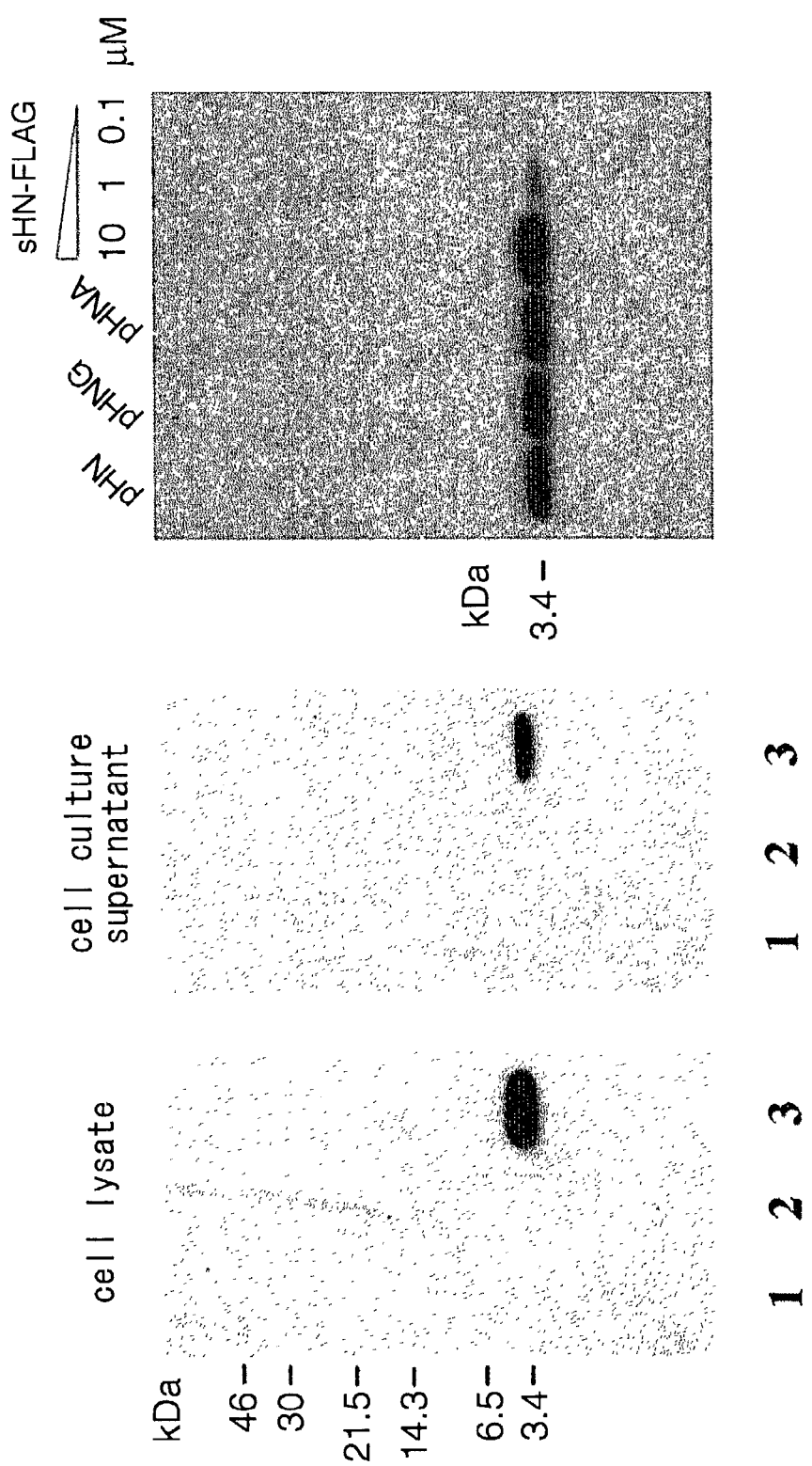

FIG. 7 depicts photographs demonstrating the immunoreactivity of HN polypeptides contained in the culture supernatant of F11 cells transfected with pHN. The left and middle panels demonstrate the result of immunoblotting using anti-FLAG antibody on cell extracts (30 µg protein) and culture supernatant (20 µl) following Tris/Tricine gel electrophoresis (lane 1: cells with no transfection; lane 2: pFLAG-transfected cells; lane 3: pHN-transfected cells). The right panel demonstrates the result of a similar analysis on the culture supernatant of cells transfected with pHN, pHNG, or pHNA. The 3 lanes on the right demonstrate the results of immunoblotting on sHN-FLAG (MAPRGFSCLLLLTSEIDLPVKRRAGT-DYKDDDDK: the underlined region is a FLAG tag) (SEQ ID NO: 6) with indicated concentrations, to determine the titer of HN polypeptides contained in the culture supernatant. Similar experiments were repeated 4 times or more.

Figure 8:
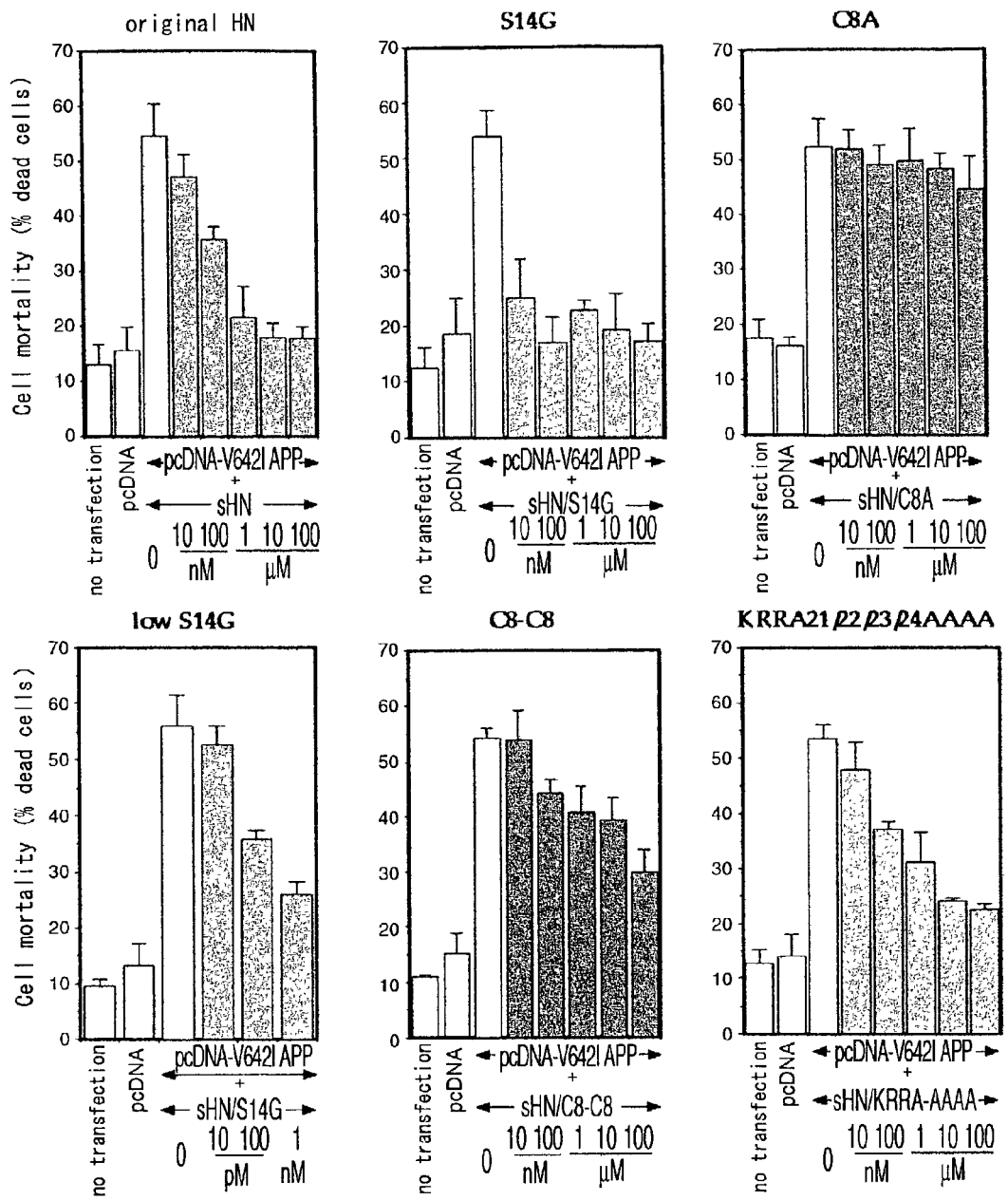

FIG. 8 depicts graphs demonstrating the effect of synthetic HN (sHN) and structural derivatives thereof on neuronal death induced by V642I APP. F11 cells were transfected with pcDNA encoding V642I APP; and were treated with various concentrations of sHN (Authentic HN) (SEQ ID NO: 5), sHNG (S14G) (SEQ ID NO: 7), sHNA (C8A) (SEQ ID NO: 8), dimer form of sHN through C8 (C8-C8), and sHN in which the C-terminal KRRA was replaced with AAAA (KRRA21/22/23/24AAAA) (SEQ ID NO: 9). 72 hours after the transfection, cell death was measured by trypan blue exclusion assay. Mean ±S.D. values of three independent experiments are indicated.

Figure 9:
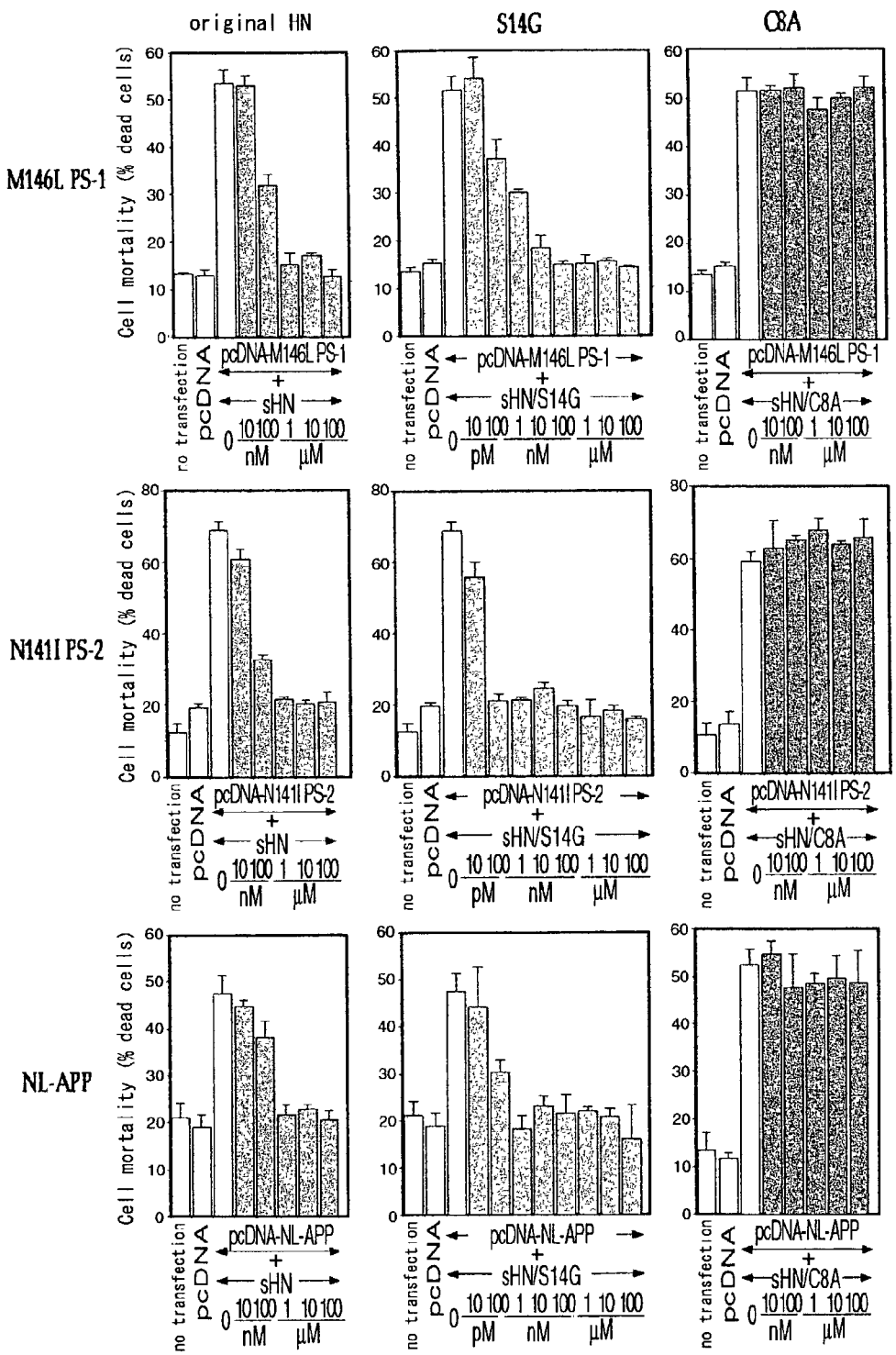

FIG. 9 depicts graphs demonstrating the effect of sHN, sHNG, or sHNA on neuronal death induced by M146L PS-1, N141I PS-2, or NL-APP. Similarly to FIG. 8, F11 cells were transfected with M146L PS-1, N141I PS-2, or NL-APP cDNA; and were treated with various concentrations of sHN (Authentic HN), sHNG (S14G), or sHNA (C8A). 72 hours after the transfection, cell death was measured by trypan blue exclusion assay. Mean ±S.D. values of three independent experiments are indicated.

Figure 10:
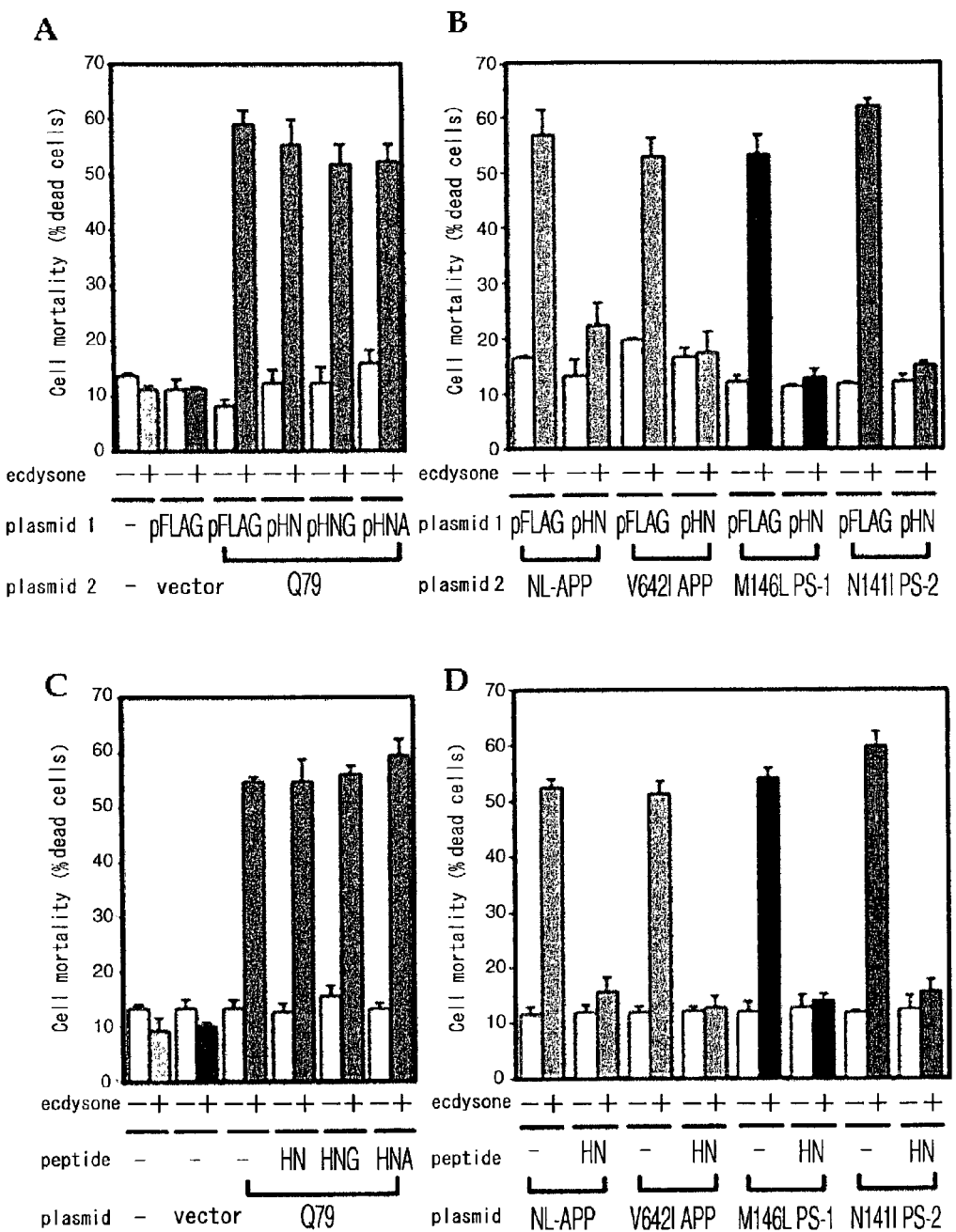

FIG. 10 depicts graphs demonstrating the lack of effect of HN and structural derivatives thereof on neuronal death induced by polyglutamine repeat Q79. Mean ±S.D. values of three independent experiments are indicated in the graphs.

Panel A: demonstrates the lack of the effect of pHN, pHNG, or pHNA on neuronal death caused by the expression of Q79 induced by ecdysone. F11/EcR cells were transfected with ecdysone-inducible type Q79 expression plasmid, and empty vector (pFLAG), pHN, pHNG, or pHNA, and were cultured for 72 hours in the presence (+) or absence (−) of ecdysone. Cell death was measured by trypan blue exclusion assay.

Panel B: demonstrates a significant suppressive effect by pHN co-transfection on neuronal death caused by ecdysone-induced expression of NL-APP, V642I APP, M146L PS-1, or N141I PS-2. Under the same conditions as in Panel A, F11/EcR cells were transfected with ecdysone-inducible FAD gene plasmid, and pFLAG or pHN, and then, were cultured for 72 hours in the presence (+) or absence (−) of ecdysone. Cell death was measured by trypan blue exclusion assay.

Panel C: demonstrates the lack of effects of sHN, sHNG, or sHNA on neuronal death induced by ecdysone-inducible expression of Q79. F11/EcR cells were transfected with ecdysone-inducible Q79 plasmids; treated with 1 µM sHN, sHNG, or sHNA; and then, were cultured in the presence (+) or absence (−) of ecdysone. 72 hours after the initiation of the ecdysone treatment, cell death was measured by trypan blue exclusion assay.

Panel D: demonstrates a significant suppressive effect by sHN on neuronal death caused by ecdysone-induced expression of NL-APP, V642I APP, M146L PS-1, or N141I PS-2. Under the same conditions as in Panel C, F11/EcR cells were transfected with ecdysone-inducible FAD gene plasmid; treated with 1M sHN; and then, were cultured in the presence (+) or absence (−) of ecdysone. 72 hours after the initiation of the ecdysone treatment, cell death was measured by trypan blue exclusion assay.

Figure 11:
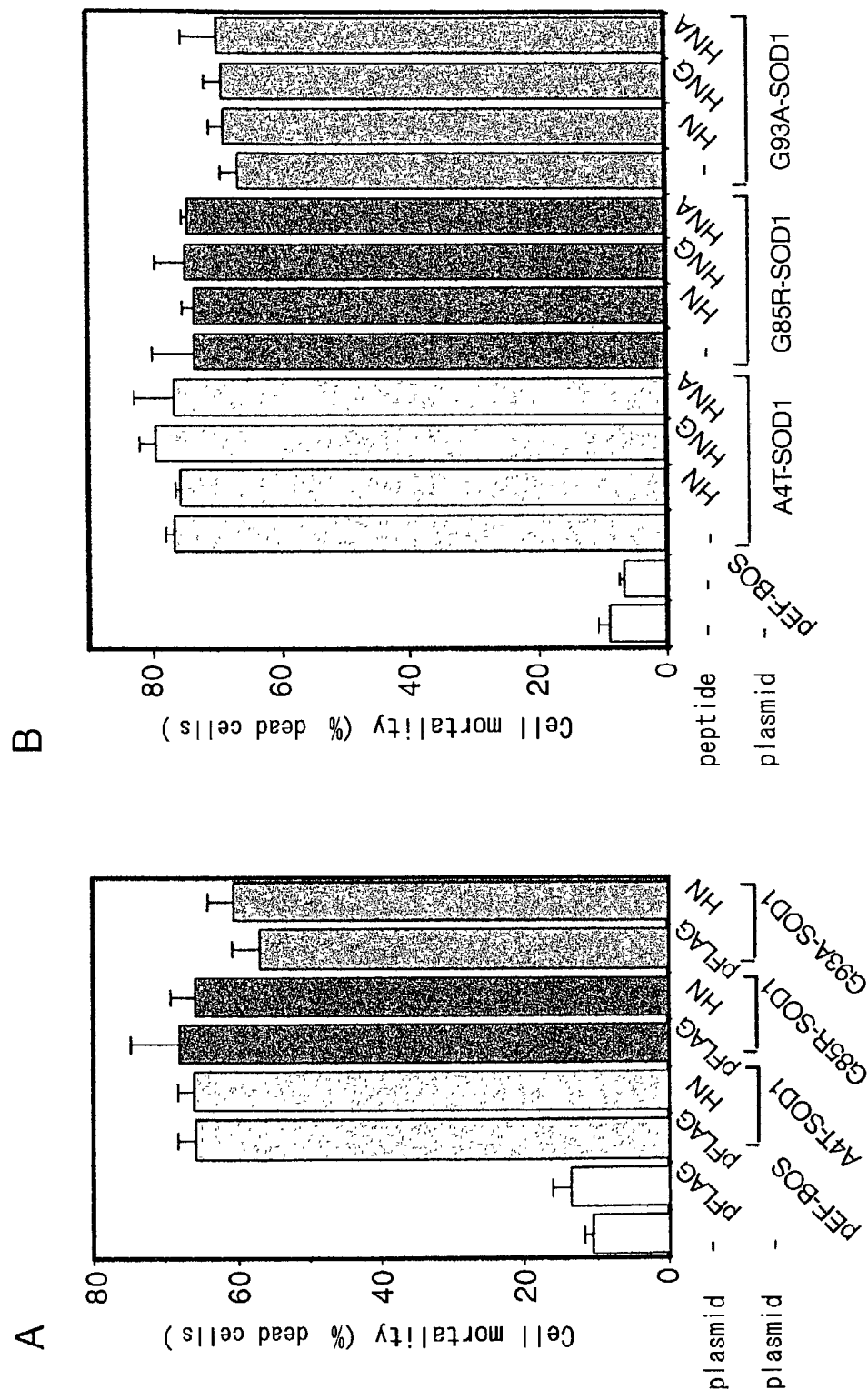

FIG. 11 depicts graphs demonstrating the lack of the effect of HN and structural derivatives thereof on neuronal death induced by the ALS-associated SOD1 mutants. Mean ±S.D. values of three independent experiments are indicated in the graphs.

Panel A: demonstrates the lack of the effect of pHN co-transfection on neuronal death induced by the expression of the ALS-related SOD1 mutants. F11 cells were transfected with pEF-BOS encoding the ALS-associated mutant SOD1 (A4T, G85R, or G93A mutants of SOD1) and empty vector (pFLAG) or pHN. Cell death was measured by trypan blue exclusion assay.

Panel B: demonstrates the lack of the effect of sHN, sHNG, or sHNA on neuronal death induced by the expression of the ALS-associated SOD1 mutants. F11 cells were transfected with pEF-BOS encoding A4T, G85R, or G93A SOD1, and were treated with 100 μM sHN, sHNG, or sHNA. Cell death was then measured by trypan blue exclusion assay.

Figure 12:
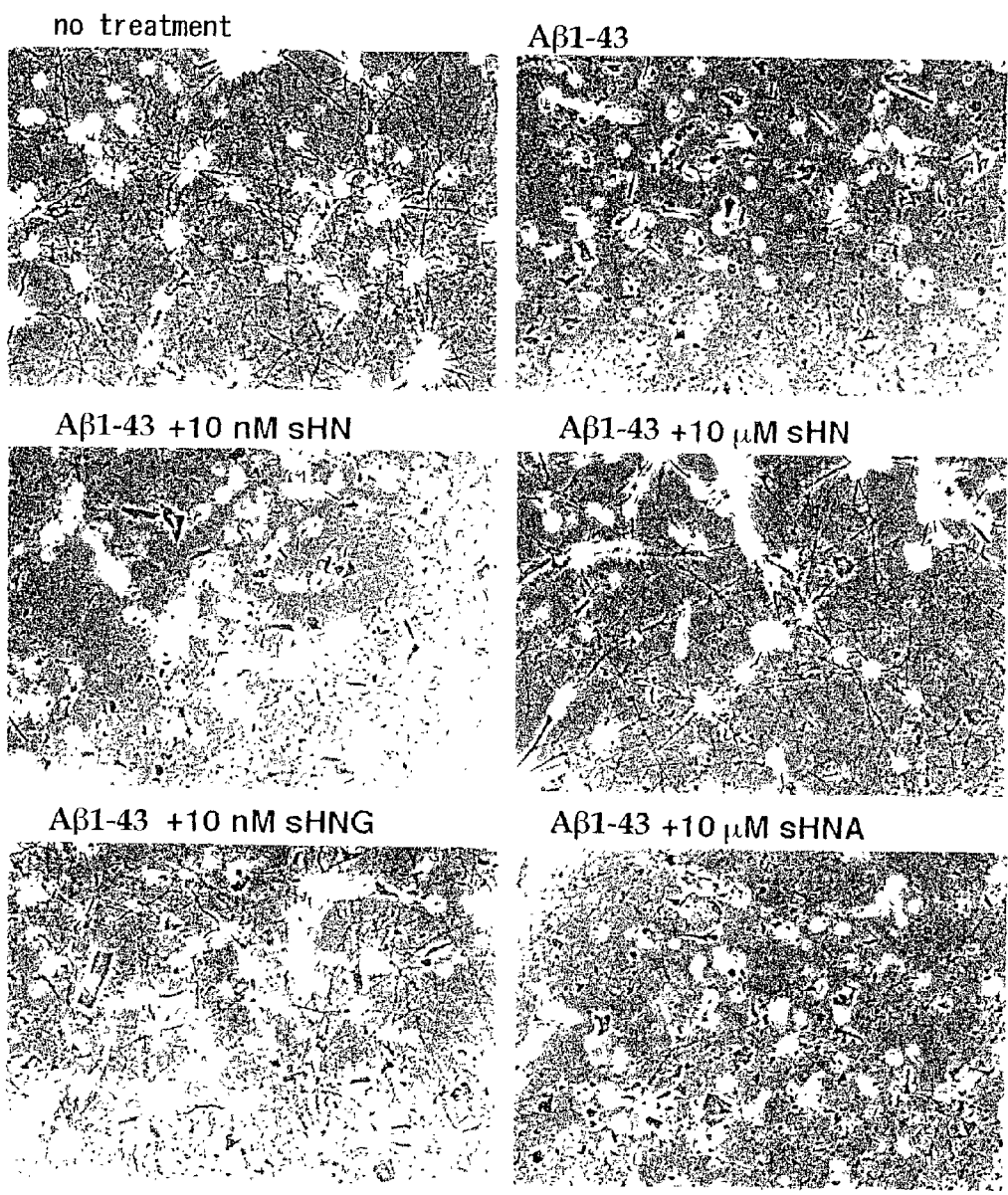

FIG. 12 depicts phase-contrast photomicrographs demonstrating the effect of HN on Aβ-induced cell death of primary cultured neurons. Representative photomicrographs are shown. Primary cultured cortical neurons were treated for 72 hours with 25 μM Aβ1-43 in the presence or absence of sHN (10 nM, 10 μM), 10 nM sHNG, or 10 μM sHNA. HN polypeptide was added 16 hours before the initiation of Aβ1-43 treatment so that the final concentrations of the polypeptides were those indicated in the figure. Addition of Aβ1-43 was performed by initially removing half of the media, and then supplementing with equal amounts of fresh media, containing 50 μM Aβ1-43 and sHN or sHNA at a concentration mentioned above. Untreated cells (no treatment), which were not treated with Aβ, were also observed. Similar experiments were performed at least 3 times, and reproducible results were obtained.

Figure 13:
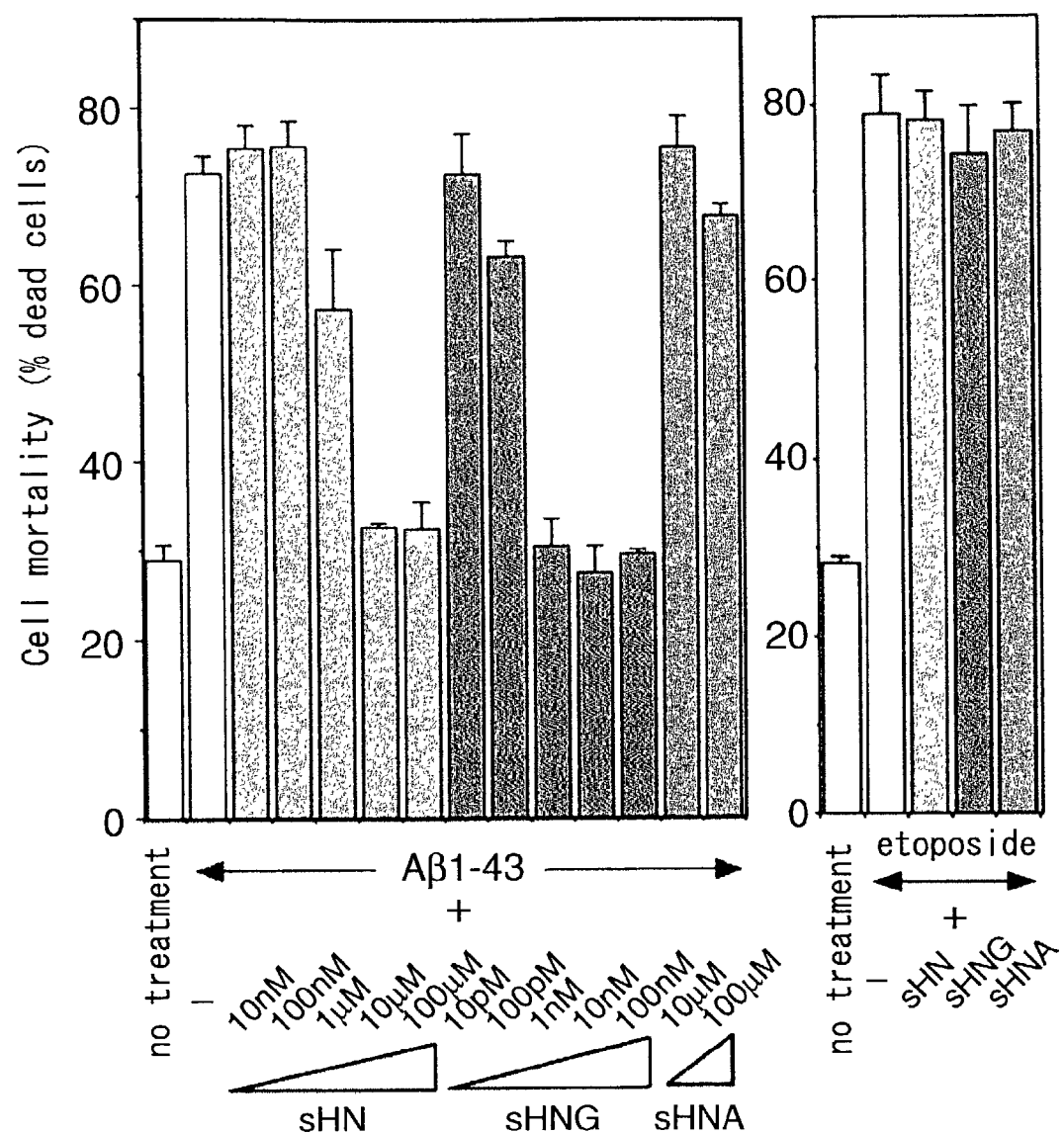

FIG. 13 depicts graphs demonstrating the effect of HN on Aβ-induced cell death of primary cultured neurons. 25 μM Aβ1-43 was added to primary cultured cortical neurons in the presence (at indicated concentrations) or absence of sHN, sHNG, or sHNA. Addition of HN polypeptides was performed similarly to that described in FIG. 12. 72 hours after the initiation of Aβ treatment, cell death was measured by trypan blue exclusion assay. Primary cultured neurons treated similarly for 72 hours with 20 μM etoposide in the presence or absence of 10 μM sHN or HN derivatives were used as the positive controls in these experiments. Similar experiments were performed at least three times, and reproducible results were obtained. Mean ±S.D. values of three independent experiments are indicated in the graphs.

Figure 14:
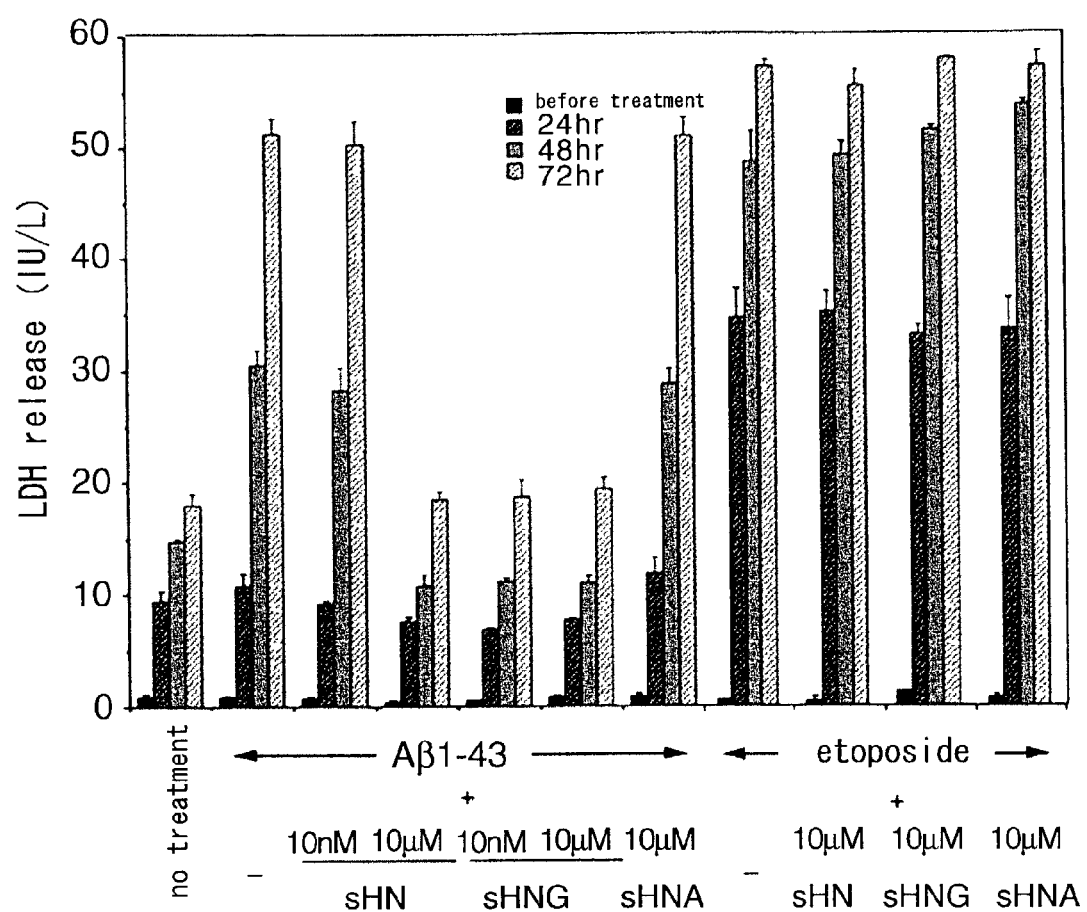

FIG. 14 depicts a graph demonstrating the effect of HN on Aβ-induced cell death of primary cultured neurons. Cell damage was monitored as the amount of LDH released into the culture media. 25 μM Aβ1-43 was added to primary cultured cortical neurons in the presence (at indicated concentrations) or absence of sHN, sHNG, or sHNA. Addition of HN polypeptides was performed similarly to that described in FIG. 12. 24, 48, or 72 hours after the initiation of Aβ treatment, the amount of LDH in the culture media was measured. LDH release from neurons treated with 20 μM etoposide in the presence or absence of HN polypeptides was also measured. Similar experiments were performed at least three times, and reproducible results were obtained. Mean ±S.D. values of three independent experiments are indicated in the graph.

Figure 15:
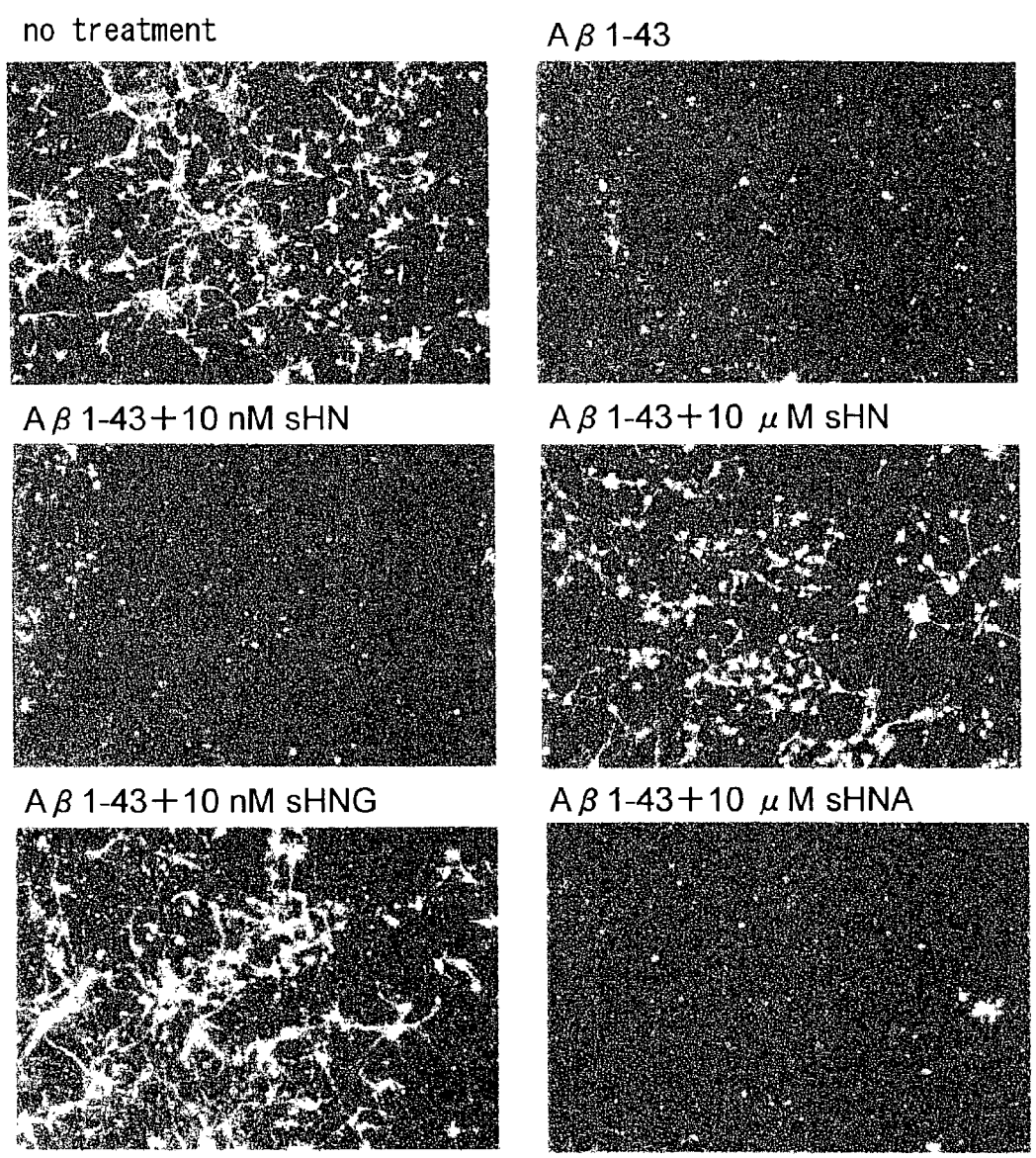

FIG. 15 depicts photographs demonstrating the effect of HN on Aβ1-43-induced cell death of primary cultured neurons. The result of Calcein-AM staining is demonstrated as fluorescence photomicrographs. 25 μM Aβ1-43 was added to primary cultured cortical neurons in the presence (at indicated final concentrations) or absence of HN polypeptides. Addition of HN polypeptides was performed similarly to that described in FIG. 12. 72 hours after Aβ1-43 treatment, calcein-AM staining was performed. Untreated cells (no treatment), that were not treated with Aβ, were also observed. Cytoplasmic fluorescence indicates cell viability. Similar experiments were performed at least three times, and reproducible results were obtained. Representative results are demonstrated in the figure.

Figure 16:
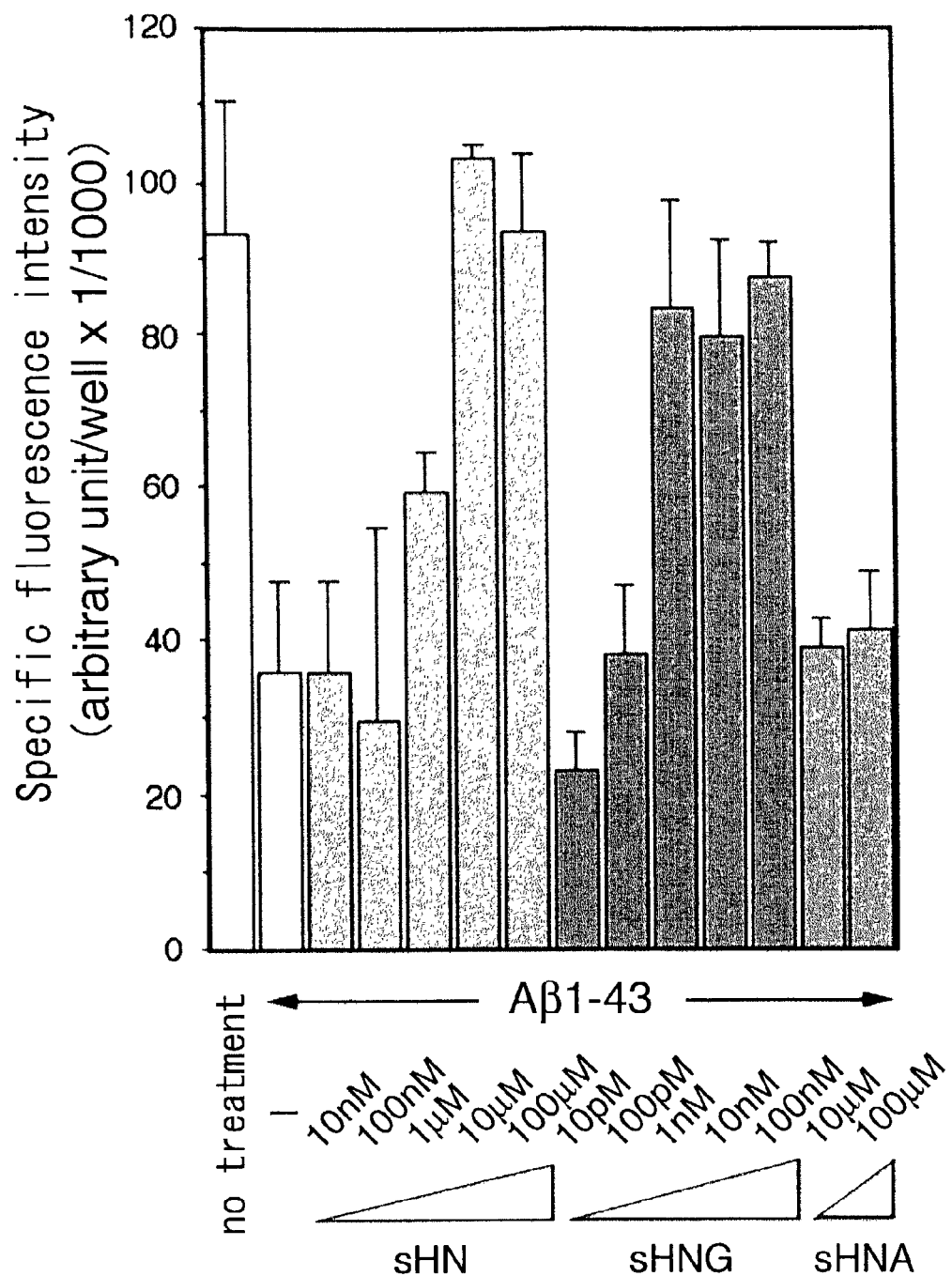

FIG. 16 depicts a graph demonstrating the result of fluorescence measurements of Calcein-AM staining. 25 μM Aβ1-43 was added to primary cultured cortical neurons in the presence (at indicated final concentrations) or absence of HN polypeptides. Addition of HN polypeptides was performed similarly to that described in FIG. 12. Calcein-AM staining was performed after 72 hours from the Aβ1-43 treatment, and fluorescence intensity of each well was measured. The basal fluorescence intensity was calculated as 36960 (unit/well), and this was subtracted from the values measured for each well. Similar experiments were performed at least three times, and reproducible results were obtained. Mean ±S.D. values of three independent experiments are indicated in the graph.

Figure 17:
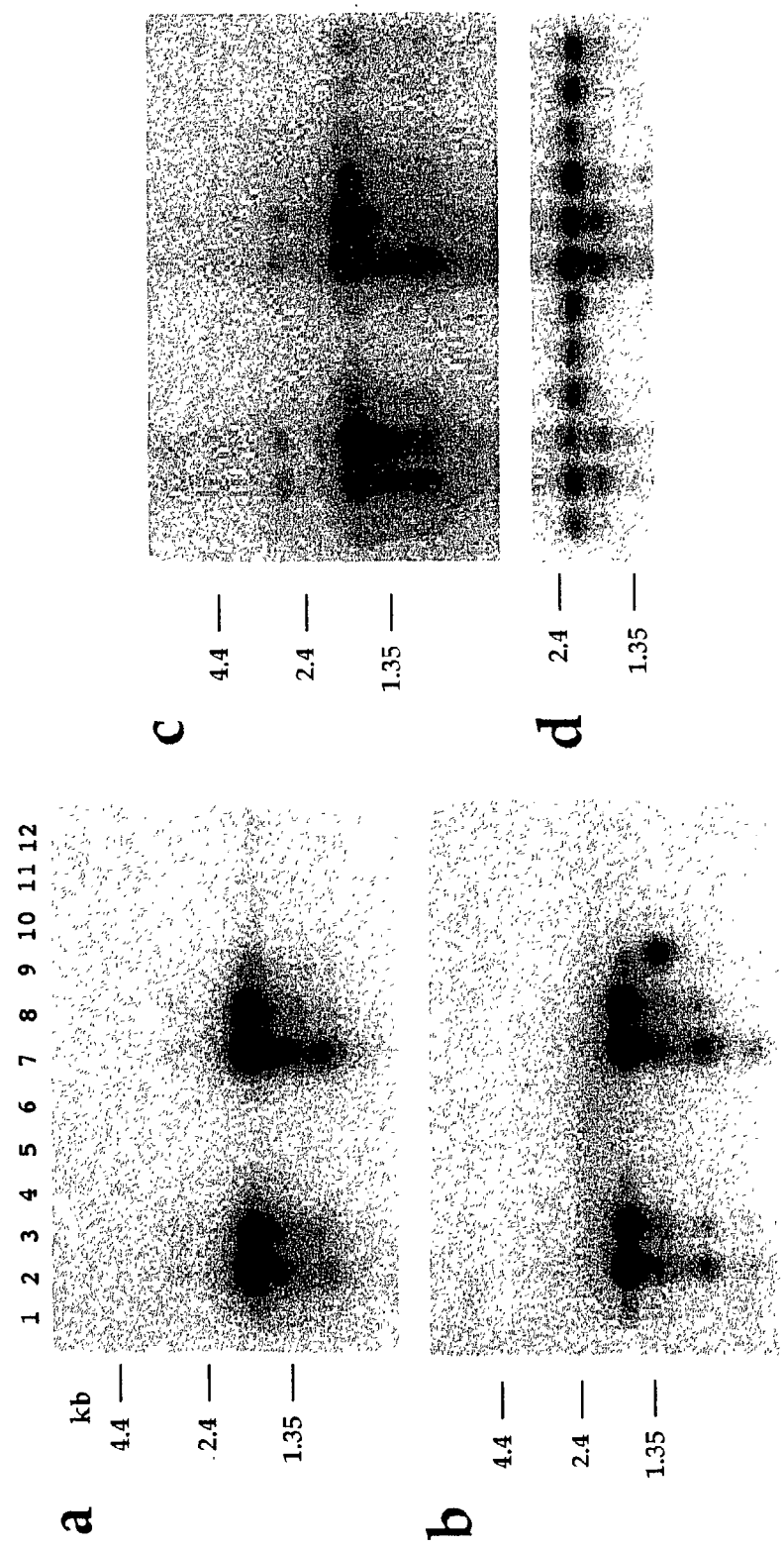

FIG. 17 depicts photographs demonstrating the expression of HN mRNA in various human tissues. Radiolabeled antisense HN (panel a), 19mer encoding the 5' region (panel b), or DT77 (panel c) was hybridized as a probe to the sheet blotted with human tissue polyA-RNA (lane 1: brain; lane 2: heart; lane 3: skeletal muscles; lane 4: large intestine; lane 5: thymus; lane 6: spleen; lane 7: kidney; lane 8: liver; lane 9: small intestine; lane 10: pancreas; lane 11: lung; lane 12: peripheral leukocytes). The result of Northern blotting on the same sheet using β-actin as the probe is shown in panel d. The numbers on the left indicate molecular sizes. Similar experiments were performed at least three times, and similar results were obtained.

Figure 18:
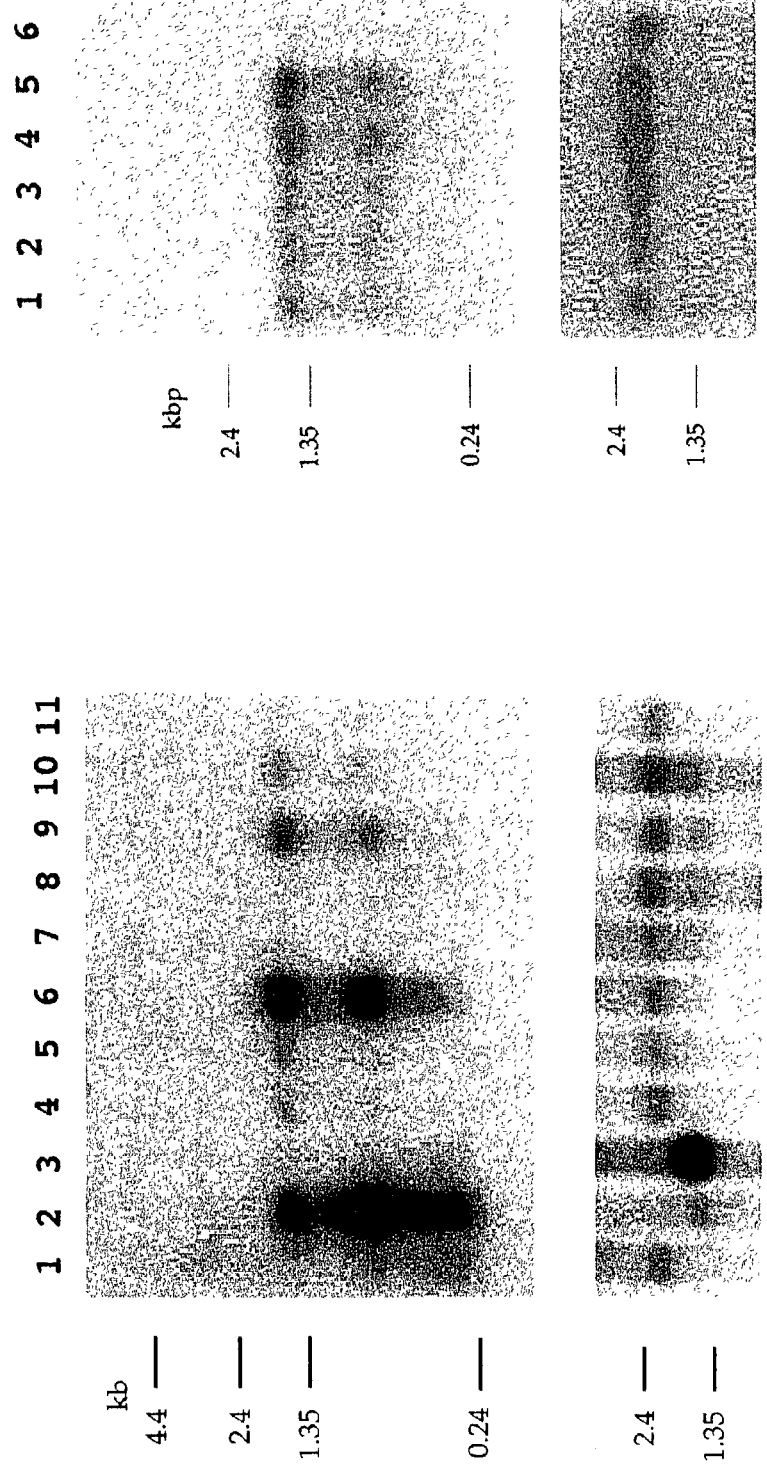

FIG. 18 depicts photographs demonstrating the expression of HN mRNA in mouse tissues. PolyA-RNA (2 μg/lane) extracted from various mouse organs was submitted to 1.2% agarose gel electrophoresis, and after blotting, hybridization was performed using labeled antisense HN (top left) or β-actin (lower left) as probes (lane 1: brain; lane 2: heart; lane 3: skeletal muscles; lane 4: thymus; lane 5: spleen; lane 6: kidney; lane 7: liver; lane 8: small intestine; lane 9: stomach; lane 10: skin; lane 11: lung).

BEST MODE FOR CARRYING OUT THE INVENTION

The present invention will be described in detail using Examples below, but the invention is not to be construed as being limited to these Examples. The experimental procedures described in these Examples are as follows:

V642I APP cDNA has been described previously (Yamatsuji, T. et al. (1996) Science 272, 1349-1352). The M146L mutant of PS-1 cDNA and the N141I mutant of PS-2 cDNA were gifts from Dr. Peter St. George-Hyslop (Sherrington, R. et al. (1995) Nature 375, 754-760) and Dr. Luciano D'Admio (Wolozin, B. et al. (1996) Science 274, 1710-1713), respectively. All of the FAD genes used in the Examples were encoded in pcDNA vectors (Funk, C. D. et al. (1990) Proc. Natl. Acad. Sci. USA, 87: 5638-5642). The ALS-associated mutant of SOD1 cDNA (A4T, G85R, G93A) (Takahashi, H. et al. (1994) Acta Neuropathol. 88, 185-8), and pDN-E/G5H-Q79 were gifts from Dr. Shoji Tsuji, (Niigata University School of Medicine, Niigata, Japan), and Dr. Akira Kakizuka (Osaka Biomedical Research Center, Osaka, Japan), respectively.

The pHN plasmids encoding Humanin were constructed by inserting HN cDNAs into the polycloning site of pFLAG-CMV-5a vectors (pFLAG) (Eastman Kodak). More specifically, pFLAG-CMV-5a plasmids were digested with EcoRI and KpnI, and the HN-encoding sense oligonucleotide (5'-AATTCACCATGGCTCCACGAGGGT-TCAGCTGTCTCTTACTTTTAACCAGTGAAATTGACC TGCCCGTGAAGAGGCGGGCAGGTAC-3'/SEQ ID NO: 1) and antisense oligonucleotide (5'-CTGCCCGCCTCT-TCACGGGCAGGTCAATTTCACTGGT-TAAAAGTAAGAGACAGCTGAACC CTCGTGGAGC-CATGGTG-3'/SEQ ID NO: 2) were ligated. The plasmid expresses Humanin polypeptide fused with FLAG tag (DYKDDDDK) to the C-terminus.

The pFLAG plasmids (pHNG and pHNA), encoding mutant HN, were constructed from pHN using Quick Change Site-directed Mutagenesis Kit (Stratagene). The sequence was confirmed by direct sequencing. Synthetic HN polypeptides (sHN) and structurally modified synthetic polypeptides purified to 95% or higher purity were used.

Synthetic HN (sHN) and several other synthetic HN-derived polypeptides were obtained from two independent sources, to obtain essentially the same results. Anti-FLAG antibody was purchased from, Eastman Kodak (M2 monoclonal antibody, Cat. #IB13010). Aβ1-43 was purchased from BACHEM (Cat. #H-1586). Other reagents were all commercially available.

F11 cells (Platika, D. et al. (1985) Proc. Natl. Acad. Sci. U.S.A. 82, 3499-3503; Yamatsuji, T. et al. (1996) Science 272, 1349-1352) were cultured in HamF-12 media containing 18% fetal bovine serum (FBS) and antibiotics. $7 \times 10^4$/well of F11 cells were seeded into a 6-well plate; cultured in HamF-12 containing 18% FBS for 12 to 16 hours; transfected 3 hours with plasmids encoding FAD genes and plasmids encoding HN (pHN, and such) by lipofection in the absence of serum (1 μg of FAD cDNA expression plasmid, 1 μg of HN cDNA expression plasmid, 4 μl of LipofectAMINE, 8 μl of Plus reagent); and then, were cultured for 2 hours in HamF-12 media containing 18% FBS. Then, culture media were exchanged with HamF-12 media containing 10% FBS; and the cells were cultured for additional 67 hours. 72 hours after transfection, cell death was measured by trypan blue exclusion assay. Experiments using synthetic HN polypeptides were conducted as follows: F11 cells (at $7 \times 10^4$/well in a 6-well plate) were transfected 3 hours with FAD genes in the absence of serum, as mentioned above; after cultivation for 2 hours in HamF-12 media containing 18% FBS, the cells were cultured for 67 hours in HamF-12 media containing 10% FBS with various concentrations of HN polypeptides; and cell death was measured by trypan blue exclusion assay. ALS-associated mutant cDNAs of SOD1 were also similarly transfected, and examined for their neurotoxicity.

To obtain the culture supernatant of F11 cells transfected with pHN (CM/F11-pHN), F11 cells were transfected with pHN in the absence of serum by lipofection for 3 hours (1 μg of pHN, 2 μl of LipofectAMINE, 4 μl of Plus reagent); and were cultured for 2 hours in HamF-12 media containing 18% FBS. Thereafter, the media was exchanged with HamF-12 media containing 10% FBS; and the cells were additionally cultured for 67 hours. CM/F11-pHN was obtained by freeze-thawing the culture media once. CM/F11-vec was similarly prepared from pFLAG-transfected F11 cells. For immunoblot analysis of CM/F11-pHN, CM/F11-pHNG, and CM/F11-pHNA, protease inhibitor cocktail (Boehringer Mannheim, Cat. #1697498; one tablet was dissolved in 2 ml of distilled water, and a volume ½5 to that of the sample was added to the sample) was added to the culture media that had not been freeze-thawed. For immunoblot analysis using cell lysates, the cells were washed twice with PBS, and were suspended in 30 μl of homogenizing buffer [10 mM tris/HCl (pH7.5), 1 mM EDTA, 1% Triton X-100, and 1 tablet/50 ml of protease inhibitor cocktail]. After two freeze-thawing cycles, the cell homogenate was centrifuged at 15,000 rpm for 10 minutes at 4° C., and the supernatant was submitted to immunoblot analysis with Tris/Tricine gel electrophoresis. Tris/Tricine gel electrophoresis was performed according to the literature (Schagger, H. and von Jagow, G. (1987) Analytical Biochemistry 166, 168-179).

F11/EcR/V642I cells were established using ecdysone-inducible V642I APP expression plasmid. First, the co-expression vector pVgRXR was transfected into F11 cells (Invitrogen) and cells were subjected to Zeocin selection to establish F11 cells (F11/EcR cells) that stably overexpress both ecdysone receptor EcR and the retinoid X receptor RXR. V642I APP cDNA was inserted into pIND vector (Invitrogen) having multiple copies of ecdysone responsive sequences; and after transfection of the vector into F11/EcR cells, G418 selection was performed. F11/EcR/V642I cells were cloned by limiting dilution. F11/EcR/V642I cells were cultured in HamF-12 media containing 18% FBS and antibiotics. Before ecdysone treatment, the cells were cultured for 24 hours in the presence of 10% FBS. Then, ecdysone (40 μM Ponasteron; Invitrogen Cat. #H101-01) was added to the cell culture media in the presence of 10% FBS. Cell death occurred to each F11/EcR/V642I cell, in response to ecdysone treatment; and the cell mortality 72 hours after treatment in all cells was 60 to 70%, which reached 80 to 90% after 96 hours from the treatment. A more detailed analysis of F11/EcR/V642I cells is described elsewhere (see International Application No. WO00/14204).

F11/EcR cell experiment using ecdysone was conducted as follows: F11/EcR cells were seeded at $7 \times 10^4$/well into a 6-well plate; cultured for 12 to 16 hours in HamF-12 media containing 18% FBS; and were similarly transfected in the absence of serum for 3 hours with 1 μg of ecdysone-inducible plasmid alone, or with 1 μg of HN-encoding plasmid, as mentioned above. After culturing for 12 to 16 hours in HamF-12 media containing 18% FBS, the cells were cultured for 2 hours in HamF-12 media containing 10% FBS, then ecdysone (Ponasterone) was added to the media (final concentration of 40 μM). Cell death was measured 72 hours after ecdysone treatment. Experiments using synthetic HN polypeptides were conducted as follows: cells were similarly transfected for 3 hours with FAD genes in the absence of serum; cultured for 12 to 16 hours in HamF-12 media containing 18% FBS; cultured for 2 hours in HamF-12 media containing 10% FBS and various concentrations of HN polypeptide; and then, 40 μM Ponasterone was added to the media. Cell death was measured by trypan blue exclusion assay after 72 hours from the ecdysone treatment. HD/SCA-associated Q79 cDNAs were also similarly transfected, and the neurotoxicity was tested.

Primary culture of mouse cortical neurons was performed in poly-D-lysine-coated 24-well plates (Sumitomo Bakelite) in the absence of serum and in the presence of N2 supplement, as described in literature (Eksioglu, Y. Z. et al. (1994) Brain Res. 644, 282-90). The purity of neurons prepared according to the method was >98%. The prepared neurons ($1.25 \times 10^5$/ well, 250 µl media/well) were preincubated in the absence or presence of 10 nM or 10 µM sHN polypeptides for 16 hours; and were treated with 25 µM Aβ1-43 in the absence or presence of sHN polypeptides at the same concentrations for 24 to 72 hours. Since primary cultured neurons are damaged even by temporary dryness during medium exchange, treatment of the cells by Aβ1-43 was performed as follows. First, half of the volume of the old medium (125 µl) was discarded. Then, 125 µl of pre-warmed fresh medium containing 50 µM Aβ1-43 and sHN with a concentration indicated above were added to the culture.

Trypan blue exclusion assay was performed as follows. Without prewashing, the cells were suspended with gentle pipetting into a serum-free media. 50 µl of 0.4% trypan blue solution (Sigma, Cat. #T-8154) were added (final concentration of 0.08%) to 200 µl cell suspension, and the suspension was mixed at room temperature. Within 3 minutes of the trypan blue solution addition, stained cells were counted. Cell mortality was determined [100−cell survival rate (%)] based on the stained cell count. LDH assay was performed using a kit (LDH-Cytotoxic Test; Wako Pure Chemical Industries, Cat. #299-50601) by sampling 6 µl of media in which neurons were cultured. Calcein staining was performed as described in literature (Bozyczko-Coyne, D. et al. (1993) Journal of Neuroscience Methods 50, 205-216). Specifically, 6 µM Calcein-AM {3',6'-Di-(O-acetyl)-2',7'-bis[N,N-bis(carboxymethyl)aminomethyl]fluorescein, tetraacetoxymethyl ester; Dojindo, Cat. #349-07201} was added to the neurons; and 30 minutes or longer after Calcein-AM treatment, fluorescence (ex=490 nm, em=515 nm) was observed by fluorescence microscopy, and measured by a spectrometer. Specific fluorescence was calculated by subtracting basal fluorescence from total fluorescence. Basal fluorescence was assigned to be the value calculated from linear trypan blue positivity-fluorescence intensity relationship, corresponding to 100% trypan blue positivity.

The assay was performed at least three times by repeating independent transfection or treatment. Student's t test was performed as the statistical analysis.

Radiolabeling of oligonucleotides for Northern blot analysis was performed using Renaissance 3' end labeling system (NEN) with terminal deoxynucleotidyl transferase (TdT). More specifically, 75 pmol of the probe oligonucleotide, 100 pmol of 3'-[$^{32}$P]-dATP (185TBq/mmol, NEN), and 36 units of TdT were incubated at 37° C. for 30 minutes; and then, the labeled oligonucleotides were separated by gel filtration. $1\times10^6$ to $5\times10^6$ cpm/µl labeled probes were obtained according to the procedure. 5'-CTG CCC GCC TCT TCA CGG GCA GGT CAA TTT CAC TGG TTA AAA GTA AGA GAC AGC TGA ACC CTC GTG GAG CCA TGT GGT G-3' (SEQ ID NO: 3) was used as the antisense HN. The cDNA fragment was radiolabeled using Ready-To-Go random labeling system (Amersham Pharmacia). Specifically, after incubation of 50 to 500 ng of denatured DNA fragments and 1.85 MBq [α-$^{32}$P] dCTP for 30 minutes at 37° C.; the labeled DNA fragments were separated by gel filtration. About $5\times10^7$ cpm/µg DNA of labeled probes were obtained by the procedure. Northern blot analysis was performed using ExpressHyb (Clontech). More specifically, after prehybridization, membranes blotted with tissue polyA$^+$-RNA (human tissue membranes obtained from Clontech; mouse tissue membranes obtained from Origene) were soaked with radiolabeled probes (2 to $5\times10^7$ cpm) for 18 hours. After washing the membrane by two steps according to the directions, the membranes were exposed to X-ray films at −70° C. using two intensifying screens.

EXAMPLE 1

Construction of cDNA Expression Library

According to the guidelines of the research institute, poly (A)$^+$RNA was extracted from a brain sample (occipital cortex) of a patient who was diagnosed through a biopsy to have sporadic Alzheimer's disease; the extracted poly(A)$^+$RNA was incorporated into an expression vector to construct a cDNA expression library. As the expression vector, the mammalian cell expression vector pEF-BOS having the elongation factor promoter (Mizushima and Nagata, 1990, Nucleic Acids Res. 18: 5322) was used. Poly(A)$^+$ RNA was reversely transcribed using a modified oligo-dT primer containing NotI site. Double-stranded cDNA was ligated with EcoRI-BstXI adaptor primers (5'-pGAA TTC ACC ACA-3' and 3'-CTT AAG GTGp-5'), and cleaved with NotI. After removing low molecular weight DNA, the cDNA was ligated with BstXI-NotI fragment of pEF-BOS, and transferred into the XL1 Blue MRF' strain by electroporation. The primary library size and the mean size of insert were $3.2\times10^6$ cfu/16 ml and 0.9 kb, respectively.

EXAMPLE 2

Identification of Humanin

The F11 cell, established by fusing E17.5 rat primary cultured neurons and mouse neuroblastoma NTG18, is an immortalized cell model of primary cultured neurons (Platika, D. et al. (1985) Proc. Natl. Acad. Sci. U.S.A. 82, 3499-3503). Without a differentiation stimulus, the cell maintains typical characteristics of primary cultured neurons, such as the production of an activation potential (Platika, D. et al. (1985) Proc. Natl. Acad. Sci. U.S.A. 82, 3499-3503). The present inventor discovered that upon transfection of F11 cells with cDNA encoding V642I/F/G APP, i.e. three kinds of FAD causative genes, transient expression of V642 mutant APP causes cell death (Yamatsuji, T. et al. (1996) Science 272, 1349-1352). Accordingly, the present inventor used the recently developed ecdysone-inducible system (No, D. et al. (1996) Proc. Natl. Acad. Sci. U.S.A. 93, 3346-51) to construct F11 clones wherein the V642I APP is inducible. F11 cells wherein the expression of V642I APP can be induced were established as follows: first, F11 clones (F11/EcR) that overexpress both ecdysone receptor and RXR were established; and then, the cells were stably transfected with pIND-V642I APP, which encodes V642I APP cDNA that is expressed by an HSV promoter placed under the control of ecdysone responsive sequences. In their original form, F11/EcR/V642I clone cells established as above hardly expresses V642I APP. However, conditional overexpression of V642I APP from the cells due to ecdysone treatment was confirmed. Furthermore, in response to ecdysone treatment, cell death was induced in all of the F11/EcR/V642I cells; and cell mortality in all F11/EcR/V642I cells reached 60 to 70% after 72 hours from the treatment, and 80 to 90% after 96 hours from the treatment.

Using these cells, and basically following the method developed by D'Adamio et al. (D'Adamio, L. et al. (1997) Semin. Immunol. 9, 17-23), "death trap screening" was performed using a modified version of the method of D'Adamio et al. In the originally described "death trap screening", Vito et al. transfected Jurkat cells with normal T-cell cDNA library; induced cell death by stimulating T-cell receptors; and collected genes that antagonize cell death. The present inventor performed death trap screening in order to screen genes that antagonize cell death induced by AD genes. The cDNA expression library comprising cDNAs prepared as described above from the brain sample of a patient with AD was transfected into F11/EcR/V642I cells, which were treated with ecdysone for 72 h, and then the plasmids were recovered from the surviving cells. The procedure was repeated 3 times, and ultimately, plasmids of about 250 clones were obtained. The clones were categorized into 36 groups that cross hybridize to each other by dot blot hybridization using respective plasmids. The largest group comprised 28 clones.

Focusing on this group of cDNAs, the present inventor sequenced all the clones. As a result, clones belonging to this group generally consisted of a cDNA having a fused sequence of 1535 bp; specifically, 5' sequence homologous to the non-coding region of Wnt-13, a 3' sequence homologous to the mitochondrial 16S ribosomal RNA, and a poly(A) region at the C-terminus. The entire sequence was novel (FIG. 1). After sequencing each clone, whether the transient transfection of respective clones significantly suppresses cell death induced by ecdysone in F11/EcR cells co-transfected with pIND-V642I APP was assayed. As a result of comparing the sequences which demonstrated a cell death suppression activity, an antagonizing activity against cell death induced by V642I APP was found to be encoded by a 75 bp open reading frame (ORF) (5'-ATGGCTCCACGAGGGTTCAGCT-GTCTCTTACTTTTAACCAGTGAAAT-TGACCTGCCCGTG AAGAGGCGGGCATGA-3'/SEQ ID NO: 4) encoding a novel 24-amino acid polypeptide "MAPRGFSCLLLLTSEIDLPVKRRA" (SEQ ID NO: 5). The present inventor dubbed the molecule Humanin (HN).

EXAMPLE 3

Suppressive Effect of Respective Clones on Cell Death Induced by FAD Genes

FIGS. 2 to 4 demonstrate the effects of co-transfection of respective clones belonging to this group. When F11/EcR cells (F11 clone stably expressing EcR and RXR, wherein the expression of genes encoded by pIND plasmid are induced by ecdysone) were transiently transfected with pIND encoding V642I APP in the absence of ecdysone (non-V642I APP inducing conditions), 72 hours later, cell death occurred in about 20% of the cells, whereas cell death occurred in a significantly high proportion (50 to 60%) of cells in the presence of ecdysone (V642I APP inducing conditions) (FIG. 2). F11/EcR cells transfected with DT63-encoding PEF-BOS, in addition to V642I APP-encoding pIND, demonstrated no significant increase of cell death induced by ecdysone even in the presence of ecdysone. On the other hand, cells transfected with PEF-BOS or pEF-BOS encoding DT171, demonstrated significant increase in cell death in response to ecdysone. FIG. 3 demonstrates the result confirming the effect of DT63 on neuronal death induced by the four FAD genes (V642I APP, NL APP, M146L PS-1, and N141I PS-2), respectively, using simple transient transfection. When F11 cells were co-transfected with empty pEF-BOS in addition to the pcDNA encoding any one of FAD genes (V642I APP, NL APP, M146L PS-1, or N141I PS-2), incubation for 72 hours lead to cell death in 50 to 70% of the cells. The transfection efficiency under this condition was about 60 to 70%, which indicates that cell death occurred after 72 hours from transfection in most of the cells expressing one of the FAD genes. Increase in cell death was dramatically suppressed by transfecting F11 cells with DT63-encoding pEF-BOS in addition to one of the FAD genes. This indicates that, DT63 cDNA antagonizes cell death induced by the four AD genes with a high efficiency. FIG. 4 demonstrates the effect of other DT clones that contain the entire HN sequence, and other DT clones that do not contain the entire sequence (DT29, DT44, and DT171 cDNA). Although marked suppression of cell death induced by each of the FAD genes was demonstrated with DT29 and DT44, which are clones encoding the entire HN sequence, action of antagonizing cell death could not be confirmed with DT171 lacking the first ATG codon of HN. These data indicate that the ORF encoded by HN protects neurons from cell death caused by all four FAD genes.

Therefore, the present inventor subcloned HN cDNA into the pFLAG vector (pHN), and directly investigated the effect of pHN towards neuronal death caused by each of the FAD genes, V642I APP, NL-APP, M146L PS-1, and N141I PS-2. As expected, transfection of pHN into F11 cells hardly showed toxicity, and furthermore, detoxified the toxicity by the FAD genes (FIG. 5). The antagonizing activity is not the result of suppression of the expression of respective FAD genes by pHN. This is verified by the fact that co-transfected pHN doesn't change the expression of FAD genes expressed from the CMV promoter, which was indicated from the finding that pHN co-transfection didn't change the expression of EGFP expressed from the CMV promoter (data not shown). Furthermore, immunoblotting of V642I APP, NL-APP, and N141I PS-2 confirmed that co-transfection of pHN hardly has any effect on the expression of these genes (data not shown).

EXAMPLE 4

Extracellular Secretion of HN

In the course of experiments, the culture supernatant of F11 cells transfected with pHN (CM/F11-pHN) was demonstrated to significantly suppress cell death induced by FAD genes encompassing V642I APP. Cell death was induced at high rates in F11 cells transfected with V642I APP cDNA under the presence of fresh media or culture supernatant of F11 cells transfected with empty pFLAG vector (CM/F11-vec), but in contrast, under the presence of CM/F11-pHN, cell death decreased dramatically in F11 cells transfected with V642I APP cDNA (FIG. 6). Similar results were obtained with DT clones. Complete suppression of V642I APP-induced cell death of F11 cells was observed with CM/DT29 and CM/DT63, but not with CM/DT171. The result indicates that HN polypeptides transcribed from HN or cDNA encoding HN are secreted into the culture media to suppress cell death induced by V642I APP. FIG. 7 demonstrates the result of investigation on immunoreactivity of HN in CM/F11-pHN using anti-FLAG antibodies. CM/F11-pHN and the lysate of cells transfected with pHN showed a single band at 3 to 4 kDa, indicating immunoreactivity of HN, the size of which concordant with the expected molecular weight for FLAG-fused HN (3837 Da; FIG. 7, left and center panels). Concentration determination using synthetic FLAG-fused HN polypeptide (MAPRGFSCLLLLTSEIDLPVKRRAGT<u>DYKDDDDK</u>: Flag tag is underlined) (SEQ ID NO: 6) demonstrated that HN is present in CM/F11-pHN at a concentration of 8 to 9 μM (FIG. 7, right panel). These findings indicate that HN is transcribed from pHN and is secreted into the culture supernatant.

EXAMPLE 5

Suppressive Effect of Synthetic HN Polypeptide on Cell Death Induced by V642I APP Next, the present inventor synthesized a synthetic HN polypeptide MAPRGFSCLLLLTSEIDLPVKRRA (SEQ ID NO: 5), and investigated its action on neuronal death induced by V642I APP by adding the polypeptide extracellularly. Cell death induced by V642I APP was dramatically suppressed by transfecting F11 cells with V642I APP cDNA and culturing the cells in the presence of 10 μM synthetic HN polypeptide (sHN) (FIG. 8). Only an extremely weak suppression was indicated at 10 nM sHN. The suppressive action was dependent on the concentration of sHN added, and at the level of 1 to 10 μM polypeptide, complete suppression could be achieved. $IC_{50}$ value was about 100 nM. The dose-dependent curve agrees with the fact that HN secreted at a level of about 10 μM into CM/F11-pHN effectively suppressed cell death induced by V642I APP.

EXAMPLE 6

Suppressive Effect of HN Polypeptide and Structural Derivatives Thereof on Cell Death Induced by V642I APP The present inventor further examined whether the cell death suppressive action of sHN is dependent on the specific primary structure (FIG. 8). A complete antagonizing effect on cell death induced by V642I APP could be observed at a concentration of 10 nM or less with S14G (MAPRGFS-CLLLLTGEIDLPVKRRA: the underlined G replaces S; called HNG) (SEQ ID NO: 7) as the polypeptide, and $IC_{50}$ of the polypeptide was about 100 μM. In contrast, C8A HN polypeptide (MAPRGFSALLLLTSEIDLPVKRRA: underlined A replaces C; called HNA) (SEQ ID NO: 8) did not significantly suppress cell death induced by V642I APP at concentrations up to 100 μM. The importance of Cys at position 8 was also suggested from the result obtained using an HN dimer (C8-C8 HN), bound through Cys at position 8. The antagonizing action level of C8-C8 HN was in between those of the original HN and HNA. On the contrary, a derivative wherein the HN C-terminal KRRA was substituted with AAAA (SEQ ID NO: 9) indicated similar functional activity to the original HN polypeptide. These results indicate that the primary structure has a fundamental role in the suppression activity of HN, and that particular amino acid residues have a predetermined role.

EXAMPLE 7

Suppressive Effect of HN Polypeptides and Structural Derivatives thereof on Cell Death Induced by FAD Genes Next, the effect of sHN, synthetic HNG (sHNG), and synthetic HNA (sHNA) on cell death induced by other FAD genes, more specifically, those induced by NL-APP, M146L PS-1, and N141I PS-2 was investigated. As indicated in FIG. 9, the original sHN demonstrated similar dose-responsiveness on cell death induced by any of the three FAD genes, and blocked neuronal death induced by the FAD genes at a concentration of 1 μM. Up to a concentration of 100 μM, sHNA did not antagonize cell death by any of the FAD genes. In contrast, sHNG completely suppressed cell death caused by any of the FAD genes at a concentration of 10 nM or less. This indicates that the action of HN is enhanced 100 to 1000 fold by S14G substitution. Taking the action of sHNG on cell death induced by V642I APP (FIG. 8) together, sHNG at a concentration of 10 nM or less, completely antagonizes neuronal death induced by all of the four different types of FAD genes.

EXAMPLE 8

Specificity of the Cell Death Suppressive Effect of HN

To elucidate the specificity of HN action, the ability of HN cDNA or HN polypeptide to antagonize cell death induced by causative genes of other neurodegenerative diseases was investigated. Polyglutamine Q79, having 72 repeats, is considered to be the cause of Huntington's disease (HD) and certain types of spinocerebellar ataxia (SCA) (Ikeda, H. et al. (1996) Nat. Genet. 13, 196-202; Kakizuka, A. (1997) Curr. Opin. Neurol. 10, 285-90). In accordance with the report that Q79 expression causes neuronal death, F11 cells underwent cell death due to the expression of Q79 (FIG. 10). Examination of neurotoxicity was carried out in the presence or absence of ecdysone by transfecting F11/EcR cells with Q79 plasmid, the expression of which is induced by ecdysone (pDN-E/G5H-Q79). In this system, cell mortality markedly increased in response to ecdysone treatment when F11/EcR cells were transfected with pDN-E/G5H-Q79 together with the empty vector (pFLAG) (FIG. 10A). Similarly, high proportions of cell death of F11/EcR cells, transfected with pDN-E/G5H-Q79 together with pHN, pHNG, or pHNA, were induced by ecdysone treatment. Further, F11/EcR cell death caused by ecdysone-induced expression of any of the FAD gene was effectively suppressed by the co-transfection of pHN (FIG. 10B). Cell death induced by Q79 was not suppressed in the experiment using sHN (FIG. 10C). Extensive cell death was caused by ecdysone when F11/EcR cells were transfected with pDN-E/G5H-Q79, even in the presence of sHN, sHNG, or sHNA at a concentration of sHN or sHNG that enables complete suppression of F11/EcR cell death caused by any one of the 4 types of FAD genes, just as in the absence of sHN, sHNG, or sHNA (FIG. 10D).

Additionally, the present inventor investigated the effect of HN on neuronal death induced by mutants of Cu/Zn-dependent superoxide dismutase (SOD1), i.e. A4T, G85R, or G93A, associated with familial amyotrophic lateral sclerosis (familial ALS). In accordance with previous reports reporting that expression of familial ALS-associated SOD1 mutants cause cell death of mammalian neurons (Rabizadeh, S. et al. (1995) Proc. Natl. Acad. Sci. U.S.A. 92, 3024-8; Ghadge, G. D. et al. (1997) J. Neurosci. 17, 8756-66), significant cell death was induced with all of the mutants by transfecting F11 cells with a cDNA that expresses one of the mutants. Further, a similar high cell mortality was induced when F11 cells were co-transfected with pHN in addition to each SOD1 mutant gene (FIG. 11A). As demonstrated in FIG. 11B, cell death caused by one of the familial ALS-associated SOD1 mutants couldn't be suppressed with 100 μM of any of sHN, sHNG, or sHNA. These data suggest that HN activates the intracellular mechanism for suppressing the cell death execution mechanism triggered by the FAD genes, but does not function on cell death caused by other neurodegenerative disease genes, and verify that the antagonizing effects of HN cDNA and HN polypeptides are common and specific to neuronal death associated with AD.

EXAMPLE 9

Suppressive Effect of HN on Cell Death of Primary Neuronal Culture

The present inventor examined the protection of primary cultured neurons by HN from damages associated with AD. Aβ is the major peptide component of senile plaque and an extracellular deposit that pathologically characterizes an AD brain, and is suggested to be associated with the pathological mechanism of AD (Selkoe, D. J. (1994) J. Neuropathol. Exp. Neurol. 53, 438-47; Cummings, J. L. et al. (1998) Neurology 51, S2-17; discussion S65-67). Aβ treatment has been reported to induce cell death of primary cultured neurons (Loo, D. T. et al. (1993) Proc. Natl. Acad. Sci. U.S.A. 90, 7951-7955; Gschwind, M. and Huber, G. (1995) J. Neurochem. 65, 292-300). As demonstrated in FIG. 12, extensive cell death accompanied by dystrophic neuritic changes of the axon was induced in primary cultured cortical neurons treated with 25 μM Aβ1-43 for 48 to 72 hours in the presence or absence of N2 supplement. Cell death induced by Aβ, as well as dystrophic neuritic changes of the axon were dramatically suppressed in primary cultured neurons pre-treated with 10 μM sHN. Cell death (measured by trypan blue exclusion; FIG. 13, left panel) and cell damage (measured by LDH released from the cells; FIG. 14) was observed by the treatment with Aβ1-43. These indices of cell survival (i.e., cell death and cell damage) were completely restored to a level observed under basal conditions by the treatment with 10 μM sHN. Under the same conditions, 100 ng/ml of NGF did not show effects to antagonize increased LDH release and cell death of neurons induced by Aβ (data not shown) In spite of the fact that sHN demonstrated a dramatic effect in antagonizing neuronal death induced by Aβ, similar treatment of neurons with 10 μM sHN could not prevent the toxic effect of 20 μM etoposide on primary cultured neurons (FIG. 13, right panel; and FIG. 14). Etoposide is an anticancer agent and has been reported to induce cell death of primary cultured neurons (Nakajima, M. et al. (1994) Brain Res. 641, 350-2). These findings support the idea that HN antagonizes neuronal death induced by Aβ1-43 by a selective mechanism. As indicated in the experiment of FAD genes using F11 cells, 10 nM sHNG completely protected cells from cell death and dystrophic neuritic changes of the axon caused by Aβ1-43, but 10 nM sHN or 10 μM sHNA both did not show any effect against neurotoxicity of Aβ (FIG. 12). The result was confirmed not only by the LDH release assay (FIG. 14), which is an assay of cell damage, and by trypan blue exclusion assay (FIG. 13), but also by Calcein staining assay (FIGS. 15 and 16), which is an assay of viable cells. Thus, HN was shown to have similar effects on primary cultured neurons as on cloned neurons. Furthermore, these data suggest the existence of a receptor (group of receptors) that specifically recognizes the HN structure, common between F11 cells and primary cultured neurons.

EXAMPLE 10

Expression of HN mRNA

Using β-actin mRNA as a positive control, expression of HN mRNA in various tissues were examined. From Northern blot analysis of human tissues, remarkable HN mRNA expression was detected in the heart, skeletal muscles, kidneys, and liver (FIG. 17a). Although less than in those tissues above, a significant expression was detected in the brain and in the gastrointestinal tract. In the immune system, including the thymus, spleen and peripheral leukocytes, mRNA was hardly detected. The size of the mainly expressed mRNA was about 1.6 kb which corresponds to the size expected for the longest DT cDNA comprising HN. Additionally, mRNAs of different sizes of about 3 kb and about 1 kb were also detected. Similar results as those mentioned above were obtained and all of the bands were detected when DT77, encoding the 3' region of HN but not the HN (see FIG. 1), or an antisense primer (GGGTGTTGAGCTTGAACGC/SEQ ID NO: 10) against the 5' region, −440 to −422, of HN was used as a probe. Thus, the mRNAs are expected to be full length HN mRNA and splicing variants thereof. The present inventor isolated several cDNAs from human heart cDNA library. The size of the isolated cDNAs exceeded 1 kbp, and the positions of the cDNAs were substantially the same as those of DT44. Similar results, except for the differences mentioned below, were obtained in mouse tissues (FIG. 18). A difference was that the skeletal muscle and liver of mouse had lower levels of HN mRNA compared to human tissues. However, quantitative differences seemed to be affected by conditions of the individuals, since the RN mRNA level was higher in skeletal muscles and liver of other mice (data not shown). Another difference was that the small 1 kb mRNA was expressed at an amount comparable or greater to the amount of the 1.6 kb mRNA in mouse heart and kidneys. Further, an additional mRNA of about 0.4 kb was specifically expressed in mouse brain, heart, and skeletal muscles. Detailed analysis of the expression regions in the brain revealed that comparatively large amounts of mRNA were expressed in the cerebellum and in the occipital lobe among the brain regions. These results indicate that HN mRNA is mainly produced in organs other than the central nervous system. Therefore, HN is possibly secreted into the blood stream, and is transported to the cranial nerves. Alternatively, locally synthesized HN in the brain may exhibit a protective action. It is interesting to note that most of the HN mRNA is synthesized in the cerebellum and occipital lobe, which are regions demonstrating strongest resistance against neuronal death in AD brains.

INDUSTRIAL APPLICABILITY

The present invention provides a method for screening suppressor genes or suppressor polypeptides for a disorder, which is characterized by screening nucleic acids or polypeptides derived from an organism suffering from a disorder that accompanies cell death. Use of a sample derived from organisms suffering from such a disorder enables the efficient cloning of suppressor genes or polypeptides for the disorder. Furthermore, the examination of suppressive effects of nucleic acids and polypeptides derived from organisms suffering from a disorder that accompanies cell death, as well as polypeptides encoded by the nucleic acids, allows the analysis of the characteristics of the nucleic acids and polypeptides.

The invention claimed is:

1. A method of screening for a candidate of a suppressor gene of Alzheimer's Disease, wherein said method comprises the steps of:
   (a) expressing in a population of cells a library of nucleic acids obtained from or synthesized from nucleic acids expressed in a tissue of a brain of an organism suffering from Alzheimer's Disease, wherein said tissue is obtained from an area of the brain showing cell death as a pathological feature of Alzheimer's Disease, and wherein said tissue comprises surviving or normal cells;
   (b) detecting a suppressive effect on Alzheimer's Disease due to the expression of a nucleic acid of the library, wherein the suppressive effect is a suppression of cell death; and,
   (c) selecting the nucleic acid having the suppressive effect; thereby identifying a candidate of a suppressor gene of Alzheimer's Disease.

2. The method according to claim 1, further comprising the step of inducing cell death, during or after step (a).

3. The method according to claim 1, wherein a plurality of nucleic acids that cause the suppressive effect are identified, further comprising:
   (d) cross-hybridizing the nucleic acids to each other to identify non-redundant groups.

4. The method according to claim 1, further comprising, prior to step (a),
   (i) obtaining the nucleic acids expressed in the tissue of the organism suffering from Alzheimer's disease; and
   (ii) constructing the library of nucleic acids therefrom.

5. The method according to claim 1, wherein said organ area is occipital cortex.

* * * * *

SEQUENCE LISTING

<160> NUMBER OF SEQ ID NOS: 10

<210> SEQ ID NO 1
<211> LENGTH: 85

<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 1
aattcaccat ggctccacga gggttcagct gtctcttact tttaaccagt gaaattgacc    60
tgcccgtgaa gaggcgggca ggtac                                         85

<210> SEQ ID NO 2
<211> LENGTH: 77
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 2
ctgcccgcct cttcacgggc aggtcaattt cactggttaa agtaagaga cagctgaacc     60 ctcgtggagc catggtg                                                  77

<210> SEQ ID NO 3
<211> LENGTH: 79
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 3
ctgcccgcct cttcacgggc aggtcaattt cactggttaa agtaagaga cagctgaacc     60 ctcgtggagc catgtggtg                                                79

<210> SEQ ID NO 4
<211> LENGTH: 75
<212> TYPE: DNA
<213> ORGANISM: Homo sapiens
<220> FEATURE:
<221> NAME/KEY: CDS
<222> LOCATION: (1)..(72)

<400> SEQUENCE: 4 atg gct cca cga ggg ttc agc tgt ctc tta ctt tta acc agt gaa att    48
Met Ala Pro Arg Gly Phe Ser Cys Leu Leu Leu Thr Ser Glu Ile
  1               5                  10                  15 gac ctg ccc gtg aag agg cgg gca tga                                75
Asp Leu Pro Val Lys Arg Arg Ala
            20

<210> SEQ ID NO 5
<211> LENGTH: 24
<212> TYPE: PRT
<213> ORGANISM: Homo sapiens

<400> SEQUENCE: 5

Met Ala Pro Arg Gly Phe Ser Cys Leu Leu Leu Thr Ser Glu Ile
  1               5                  10                  15

Asp Leu Pro Val Lys Arg Arg Ala
            20

<210> SEQ ID NO 6
<211> LENGTH: 34
<212> TYPE: PRT

```
<213> ORGANISM: Artificial Sequence
<220> FEATURE:
<223> OTHER INFORMATION: Description of Artificial Sequence:
      artificially synthesized sequence (sHN-FLAG)

<400> SEQUENCE: 6

Met Ala Pro Arg Gly Phe Ser Cys Leu Leu Leu Leu Thr Ser Glu Ile
 1               5                  10                  15

Asp Leu Pro Val Lys Arg Arg Ala Gly Thr Asp Tyr Lys Asp Asp Asp
            20                  25                  30

Asp Lys

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence:
      artificially synthesized sequence (HNG)

<400> SEQUENCE: 7

Met Ala Pro Arg Gly Phe Ser Cys Leu Leu Leu Leu Thr Gly Glu Ile
 1               5                  10                  15

Asp Leu Pro Val Lys Arg Arg Ala
            20

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence:
      artificially synthesized sequence (HNA)

<400> SEQUENCE: 8

Met Ala Pro Arg Gly Phe Ser Ala Leu Leu Leu Leu Thr Ser Glu Ile
 1               5                  10                  15

Asp Leu Pro Val Lys Arg Arg Ala
            20

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 9

Met Ala Pro Arg Gly Phe Ser Cys Leu Leu Leu Leu Thr Ser Glu Ile
 1               5                  10                  15

Asp Leu Pro Val Ala Ala Ala Ala
            20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 10
gggtgttgag cttgaacgc                                              19
```